US012747446B2

(12) United States Patent
Gao et al.

(10) Patent No.: US 12,747,446 B2
(45) Date of Patent: Sep. 29, 2026

(54) ENGINEERED REGULATOR FOR IMPROVED PLANT OIL YIELD

(71) Applicant: Nanyang Technological University, Singapore (SG)

(72) Inventors: Yonggui Gao, Singapore (SG); Wei Ma, Singapore (SG); Zhu Qiao, Singapore (SG); Que Kong, Singapore (SG)

(73) Assignee: Nanyang Technological University, Singapore (SG)

( * ) Notice: Subject to any disclaimer, the term of this patent is extended or adjusted under 35 U.S.C. 154(b) by 183 days.

(21) Appl. No.: 18/695,479

(22) PCT Filed: Sep. 22, 2022

(86) PCT No.: PCT/SG2022/050683
§ 371 (c)(1),
(2) Date: Mar. 26, 2024

(87) PCT Pub. No.: WO2023/055291
PCT Pub. Date: Apr. 6, 2023

(65) Prior Publication Data

US 2025/0115925 A1 Apr. 10, 2025

(30) Foreign Application Priority Data

Sep. 30, 2021 (SG) ........................... 10202110937Q
Jun. 1, 2022 (SG) ............................ 10202250129P

(51) Int. Cl.
*C12N 15/82* (2006.01)
*C07K 14/415* (2006.01)

(52) U.S. Cl.
CPC ........ *C12N 15/8247* (2013.01); *C07K 14/415* (2013.01)

(58) Field of Classification Search
CPC .................................................. C12N 15/8247
See application file for complete search history.

(56) References Cited

U.S. PATENT DOCUMENTS

2017/0218386 A1 8/2017 Msu
2018/0094274 A1* 4/2018 Benning .............. C07K 14/415

OTHER PUBLICATIONS

Keskin et al., 2004, A new, structurally nonredundant, diverse data set of protein-protein interfaces and its implications, Protein Science 13: 1043-1055. (Year: 2004).*
Guo et al., 2004, Protein tolerance to random amino acid change, Proceedings of the National Academy of Sciences USA 101: 9205-9210. (Year: 2004).*
Thornton et al., 2000, From structure to function: approaches and limitations, Nature Structural Biology, structural genomic supplement, Nov. 2000: 991-994. (Year: 2000).*
Kong et al., 2019, WRINKLED1, a "Master Regulator" in Transcriptional Control of Plant Oil Biosynthesis, Plants 8, 238: 1-10. (Year: 2019).*
Zhai Z. et al., Phosphorylation of WRINKLED1 by KIN10 Results in Its Proteasomal Degradation, Providing a Link between Energy Homeostasis and Lipid Biosynthesis. Plant Cell., Mar. 17, 2017, vol. 29, No. 4, pp. 871-889.
Qiao Z. et al., Molecular basis of the key regulator WRINKLED1 in plant oil biosynthesis. Science Advances, Aug. 24, 2022, vol. 8, No. 34, pp. 1-10.

* cited by examiner

*Primary Examiner* — Weihua Fan
*Assistant Examiner* — Yanxin Shen
(74) *Attorney, Agent, or Firm* — Lisa Mueller; Casimir Jones SC

(57) ABSTRACT

The present invention relates to isolated polynucleotides or polypeptides that lead to improved plant oil yields. Disclosed herein is an isolated polynucleotide encoding a polypeptide that is distinguished from a wild-type Wrinkledt polypeptide by at least one amino acid substitution in the wild-type Wrinkledt amino acid sequence. In an embodiment, the at least one amino acid substitution comprises an amino acid substitution at a position corresponding to position 74 as set forth in SEQ ID NO: 1. In another embodiment, the substitution at position 74 is an amino acid substitution to a positively charged residue, wherein the positively charged residue is arginine or lysine.

11 Claims, 11 Drawing Sheets

Specification includes a Sequence Listing.

SEQUENCE LISTING

Sequence total quantity: 26

SEQ ID NO: 1 moltype = AA length = 430

FEATURE Location/Qualifiers

```
source                 1..430
                       mol_type = protein
                       organism = synthetic construct
SEQUENCE: 1
MKKRLTTSTC SSSPSSSVSS STTTSSPIQS EAPRPKRAKR AKKSSPSGDK SHNPTSPAST  60
RRSSIYRGVT RHRWTGRFEA HLWDKSSWNS IQNKKGKQVY LGAYDSEEAA AHTYDLAALK  120
YWGPDTILNF PAETYTKELE EMQRVTKEEY LASLRRQSSG FSRGVSKYRG VARHHHNGRW  180
EARIGRVFGN KYLYLGTYNT QEEAAAAYDM AAIEYRGANA VTNFDISNYI DRLKKKGVFP  240
FPVNQANHQE GILVEAKQEV ETREAKEEPR EEVKQQYVEE PPQEEEEKEE EKAEQQEAEI  300
VGYSEEAAVV NCCIDSSTIM EMDRCGDNNE LAWNFCMMDT GFSPFLTDQN LANENPIEYP  360
ELFNELAFED NIDFMFDDGK HECLNLENLD CCVVGRESPP SSSSPLSCLS TDSASSTTTT  420
TTSVSCNYLV                                                         430

SEQ ID NO: 2           moltype = AA  length = 430
FEATURE                Location/Qualifiers
source                 1..430
                       mol_type = protein
                       organism = synthetic construct
SEQUENCE: 2
MKKRLTTSTC SSSPSSSVSS STTTSSPIQS EAPRPKRAKR AKKSSPSGDK SHNPTSPAST  60
RRSSIYRGVT RHRWTGRFEA HLWDKSSWNS IQNKKGKQVY LGAYDSEEAA AHTYDLAALK  120
YWGPDTILNF PAETYTKELE EMQRVTKEEY LASLRRQSSG FSRGVSKYRG VARHHHNGRW  180
EARIGRVFGN KYLYLGTYNT QEEAAAAYDM AAIEYRGANA VTNFDISNYI DRLKKKGVFP  240
FPVNQANHQE GILVEAKQEV ETREAKEEPR EEVKQQYVEE PPQEEEEKEE EKAEQQEAEI  300
VGYSEEAAVV NCCIDSSTIM EMDRCGDNNE LAWNFCMMDT GFSPFLTDQN LANENPIEYP  360
ELFNELAFED NIDFMFDDGK HECLNLENLD CCVVGRESPP SSSSPLSCLS TDSASSTTTT  420
TTSVSCNYLV                                                         430

SEQ ID NO: 3           moltype = AA  length = 430
FEATURE                Location/Qualifiers
source                 1..430
                       mol_type = protein
                       organism = synthetic construct
SEQUENCE: 3
MKKRLTTSTC SSSPSSSVSS STTTSSPIQS EAPRPKRAKR AKKSSPSGDK SHNPTSPAST  60
RRSSIYRGVT RHRWTGRFEA HLWDKSSWNE GKNKKGKQVY LGAYDSEEAA AHTYDLAALK  120
YWGPDTILNF PAETYTKELE EMQRVTKEEY LASLRRQSSG FSRGVSKYRG VARHHHNGRW  180
EARIGRVFGN KYLYLGTYNT QEEAAAAYDM AAIEYRGANA VTNFDISNYI DRLKKKGVFP  240
FPVNQANHQE GILVEAKQEV ETREAKEEPR EEVKQQYVEE PPQEEEEKEE EKAEQQEAEI  300
VGYSEEAAVV NCCIDSSTIM EMDRCGDNNE LAWNFCMMDT GFSPFLTDQN LANENPIEYP  360
ELFNELAFED NIDFMFDDGK HECLNLENLD CCVVGRESPP SSSSPLSCLS TDSASSTTTT  420
TTSVSCNYLV                                                         430

SEQ ID NO: 4           moltype = AA  length = 430
FEATURE                Location/Qualifiers
source                 1..430
                       mol_type = protein
                       organism = synthetic construct
SEQUENCE: 4
MKKRLTTSTC SSSPSSSVSS STTTSSPIQS EAPRPKRAKR AKKSSPSGDK SHNPTSPAST  60
RRSSIYRGVT RHRWTGRFEA HLWDKSSWNS IQNKKGKQVY LGAYDSEEAA AHTYDLAALK  120
YWGPDTILNF PAETYTKELE EMQRVTKEEY LASLRRQSSG FSRGVSKYRG VARQQKNGRW  180
EARIGRVFGN KYLYLGTYNT QEEAAAAYDM AAIEYRGANA VTNFDISNYI DRLKKKGVFP  240
FPVNQANHQE GILVEAKQEV ETREAKEEPR EEVKQQYVEE PPQEEEEKEE EKAEQQEAEI  300
VGYSEEAAVV NCCIDSSTIM EMDRCGDNNE LAWNFCMMDT GFSPFLTDQN LANENPIEYP  360
ELFNELAFED NIDFMFDDGK HECLNLENLD CCVVGRESPP SSSSPLSCLS TDSASSTTTT  420
TTSVSCNYLV                                                         430

SEQ ID NO: 5           moltype = DNA  length = 24
FEATURE                Location/Qualifiers
source                 1..24
                       mol_type = other DNA
                       organism = synthetic construct
SEQUENCE: 5
tacttcctcg gtttcatcgt ccac                                         24

SEQ ID NO: 6           moltype = DNA  length = 24
FEATURE                Location/Qualifiers
source                 1..24
                       mol_type = other DNA
                       organism = synthetic construct
SEQUENCE: 6
atgaaggagc caaagtagca ggtg                                         24

SEQ ID NO: 7           moltype = AA  length = 413
FEATURE                Location/Qualifiers
source                 1..413
                       mol_type = protein
                       organism = synthetic construct
```

-continued

```
SEQUENCE: 7
MKRPLTTSPS SSSSTSSSAC ILPTQSETPR PKRAKRAKKS SLRSDVKPQN PTSPASTRRS  60
SIYRGVTRHR WTGRYEAHLW DKSSWNSIQN KKGKQVYLGA YDSEEAAAHT YDLAALKYWG  120
PNTILNFPVE TYTKELEEMQ RCTKEEYLAS LRRQSSGFSR GVSKYRGVAR HHHNGRWEAR  180
IGRVFGNKYL YLGTYNTQEE AAAAYDMAAI EYRGANAVTN FDIGNYIDRL KKKGVFPFPV  240
SQANHQEAVL AETKQEVEAK EEPTEEVKQC VEKEEAKEEK TEKKQQQEVE EAVITCCIDS  300
SESNELAWDF CMMDSGFAPF LTDSNLSSEN PIEYPELFNE MGFEDNIDFM FEEGKQDCLS  360
LENLDCCDGV VVVGRESPTS LSSSPLSCLS TDSASSTTTT ATTVTSVSWN YSV         413

SEQ ID NO: 8           moltype = AA  length = 395
FEATURE                Location/Qualifiers
source                 1..395
                       mol_type = protein
                       organism = synthetic construct
SEQUENCE: 8
MERSQRQSPP PPSPSSSSSS VSADTVLVPP GKRRRAATAK AGAEPNKRIR KDPAAAAAGK  60
RSSVYRGVTR HRWTGRFEAH LWDKHCLAAL HNKKKGRQVY LGAYDSEEAA ARAYDLAALK  120
YWGPETLLNF PVEDYSSEMP EMEAVSREEY LASLRRRSSG FSRGVSKYRG VARHHHNGRW  180
EARIGRVFGN KYLYLGTFDT QEEAAKAYDL AAIEYRGVNA VTNFDISCYL DHPLFLAQLQ  240
QEPQVVPALN QEPQPDQSET GTTEQEPESS EAKTPDGSAE PDENAVPDDT AEPLSTVDDS  300
IEEGLWSPCM DYELDTMSRP NFGSSINLSE WFADADFDCN IGCLFDGCSA ADEGSKDGVG  360
LADFSLFEAG DVQLKDVLSD MEEGIQPPAM ISVCN                             395

SEQ ID NO: 9           moltype = AA  length = 393
FEATURE                Location/Qualifiers
source                 1..393
                       mol_type = protein
                       organism = synthetic construct
SEQUENCE: 9
MTMERSQPQH QQSPPSPSSS SSCVSADTVL VPPGKRRRRA ATAKANKRAR KDPSDPPPAA  60
GKRSSVYRGV TRHRWTGRFE AHLWDKHCLA ALHNKKKGRQ VYLGAYDGEE AAARAYDLAA  120
LKYWGPEALL NFPVEDYSSE MPEMEAASRE EYLASLRRRS SGFSRGVSKY RGVARHHHNG  180
RWEARIGRVL GNKYLYLGTF DTQEEAAKAY DLAAIEYRGA NAVTNFDISC YLDHPLFLAQ  240
LQQEQPQVVP ALDQEPQADQ REPETTAQEP VSSQAKTPAD DNAEPDDIAE PLITVDNSVE  300
ESLWSPCMDY ELDTMSRSNF GSSINLSEWF TDADFDSDLG CLFDGRSAVD GGSKGGVGVA  360
DFSLFEAGDG QLKDVLSDME EGIQPPTIIS VCN                               393

SEQ ID NO: 10          moltype = AA  length = 417
FEATURE                Location/Qualifiers
source                 1..417
                       mol_type = protein
                       organism = synthetic construct
SEQUENCE: 10
MKRSSASSCS SSSSSSSPS SSSSSACSAS SSCLDSVSPP NHHQLRSENS KSKRIRKIQT  60
KQDKCQTTAT TTSPSGGGRR SSIYRGVTRH RWTGRFEAHL WDKSSWNNIQ NKKGRQVYLG  120
AYDNEEAAAH TYDLAALKYW GQDTTLNFLI ETYSKELEEM QKMSKEEYLA SLRRRSSGFS  180
RGVSKYRGVA RHHHNGRWEA RIGRVFGNKY LYLGTYNTQE EAAAAYDMAA IEYRGANAVT  240
NFDVSHYIDR LKKKGIPLDK ILPETLSKGS KESEEIERTS PLPLPSPPSP SITPLHEEIV  300
SPQLLETECP QHPPCMDTCT TIVMDPIEEH ELTWSFCLDS GLVPLPAPDL PLANGCELPD  360
LLDDTGFEDN IDLIFDACRF GNDANPADEN GKERLSSAST SPSCSTTLTS VSCNYSV      417

SEQ ID NO: 11          moltype = AA  length = 433
FEATURE                Location/Qualifiers
source                 1..433
                       mol_type = protein
                       organism = synthetic construct
SEQUENCE: 11
MKRRLTSTNS SSSSPSSSVS SSTTTSSPIQ SETPRPKRAN KRAKKPSPSD DKTTNPTSPA  60
STRRSSIYRG VTRHRWTGRF EAHLWDKSSW NSIQNKKGKQ VYLGAYDSEE AAAHTYDLAA  120
LKYWGPDTIL NFPAETYTKE LEEMQRVTKE EYLASLRRQS SGFSRGVSKY RGVARHHHNG  180
RWEARIGRVF GNKYLYLGTY NTQEEAAAAY DMAAIEYRGA NAVTNFDISN YIDRLKKKGV  240
FPFPVSQANH QEEAILAEAK QEIEAKEEPT EEVKQQCVEE PPQVQKEEKA EQQGEEVVGY  300
KEEEAAVVNC CIDSSAIMEM NRCSNDNELA WNFCMMDSGF TPFLTDQNLS NENPIEYPEL  360
FNELAFEENI DFMFEEGKNE CLGLGNLDCC EVVVGRESPT SSSSPLSCFS TDSASSTTTT  420
TATTTSVSCN YSV                                                     433

SEQ ID NO: 12          moltype = AA  length = 431
FEATURE                Location/Qualifiers
source                 1..431
                       mol_type = protein
                       organism = synthetic construct
SEQUENCE: 12
MKRRLTSTNS SSSSPSSSVS SSTTTSSPIQ SETPRPKRAN KRAKKPSPSG DKPNNPTSPA  60
STRRSSIYRG VTRHRWTGRF EAHLWDKSSW NSIQNKKGKQ VYLGAYDSEE AAAHTYDLAA  120
LKYWGPDTIL NFPAETYTKE LEEMQRVTKE EYLASLRRQS SGFSRGVSKY RGVARHHHNG  180
RWEARIGRVF GNKYLYLGTY NTQEEAAAAY DMAAIEYRGA NAVTNFDISN YIDRLKKKGV  240
YPFPVSQANH QEEAILAEAK QEIEAKEEPT EEVKQQYVEE PPQQVQKEEK AEQQGEEFVA  300
YKEEEAAVVN CCIDSSAIMG MNRCSDDNEL AWNFCMMDSG FAPFLTDQNL PNENPIEYPE  360
LFNELAFEEN IDFMFEEGKN EYLGLGNLDC CDVVVVGRES PTSSSSPLSC FSTDSASSST  420
```

```
TTTSVSCNYS V                                                431

SEQ ID NO: 13          moltype = AA  length = 434
FEATURE                Location/Qualifiers
source                 1..434
                       mol_type = protein
                       organism = synthetic construct
SEQUENCE: 13
MKRRLTSTNS SSSSPSSSVS SSTTTSSPIQ SETPRPKRAN KRAKKPSPSD DKPNNPTSPA  60
STRRSSIYRG VTRHRWTGRF EAHLWDKSSW NSIQNKKGKQ VYLGAYDSEE AAAHTYDLAA  120
LKYWGPDTIL NFPAETYTKE LEEMQRVTKE EYLASLRRQS SGFSRGVSKY RGVARHHHNG  180
RWEARIGRVF GNKYLYLGTY NTQEEAAAAY DMAAIEYRGA NAVTNFDISN YIDRLKKKGV  240
FPFPVSQANH QEEAILAEAK QEIEAKEEPT EEVKQQCVEE PPQVQKEEKA EQQGEEFVGY  300
NKEEEATVVN CSIDSSAIME MNRCSDDNEL AWNFCMMDSG FAPFLTDQNL SNENPIEYPE  360
LFNELAFEEN IDFMFEEGKN ECLGLGNMDC CDVVVVGRES PTSSSSPLSC FSTDSASSTT  420
TATTTTSVSC NYSV                                             434

SEQ ID NO: 14          moltype = AA  length = 420
FEATURE                Location/Qualifiers
source                 1..420
                       mol_type = protein
                       organism = synthetic construct
SEQUENCE: 14
MKRSPPQPSP SPSSSPASSS SSPSSSDSSS SIAIPRKRAR TAAAAAGGGK ARAAAAKRPK  60
KDGKDSGSSS NGGGGGGGKR SSIYRGVTRH RWTGRFEAHL WDKNCFTSLQ NKKKGRQVYL  120
GAYDTEEAAA RAYDLAALKY WGPETTLNFS ADDYGKERSE MEAVSREEYL AALRRRSSGF  180
SRGVSKYRGV ARHHHNGRWE ARIGRVLGNK YLYLGTFDTQ EEAARAYDLA AIQYRGANAV  240
TNFDISRYLD QPQLLEQLQQ QQGPQVVAAL QEEAQRDHQS DNAVQELNSG EAQTPGGIDE  300
PIAIGDSTED INTSLTVDDI IEESLWSPYE FDIMAGVNVS NSMNLSELFS DVAFEGNIGC  360
LFEECSGIDD CSSRHGAGLA AFGLFTEGDD KLKDVSEMEM EVNPQANDVS CPPKMITVCN  420

SEQ ID NO: 15          moltype = AA  length = 426
FEATURE                Location/Qualifiers
source                 1..426
                       mol_type = protein
                       organism = synthetic construct
SEQUENCE: 15
MKRSPASSCS SSTSSVGFEV HHPIEKRRPK HPRRNNLKSQ KCKQNQTTTG GRRSSIYRGV  60
TRHRWTGRFE AHLWDKSSWN NIQSKKGKQV YLGAYDTEES AARTYDLAAL KYWGKDATLN  120
FPIETYTKDL EEMDKVSREE YLASLRRQSS GFSRGISKYR GVARHHHNGR WEARIGRVCG  180
NKYLYLGTYK TQEEAAVAYD MAAIEYRGVN AVTNFDISNY MDKIKKKNDQ TLQQQQTEVQ  240
TETVPNSSDS EEAEVEQQHT TTITTPPPSE NLHMLPQEHQ VQYTHHVTPR DEESSSLVTI  300
MEHVLEQDLP WSFMYTGLSQ FQDPNLALSK GDDDLAGMFD GAGFEEDIDF LFSTQPGDHE  360
TESDVNNMSA VLDSVECGDT NGAGGRSMVY HHVDNNNKQK KMLSFASSSS PSSTTTTVSC  420
DYALDL                                                      426

SEQ ID NO: 16          moltype = AA  length = 412
FEATURE                Location/Qualifiers
source                 1..412
                       mol_type = protein
                       organism = synthetic construct
SEQUENCE: 16
MKRSPASSCS SSTSSVGFEA PIEKRRPKHP RRNNLKSQKC KQNQTTTGGR RSSIYRGVTR  60
HRWTGRFEAH LWDKSSWNNI QSKKGRQVYL GAYDTEESAA RTYDLAALKY WGKDATLNFP  120
IETYTKELEE MDKVSREEYL ASLRRQSSGF SRGLSKYRGV ARHHHNGRWE ARIGRVCGNK  180
YLYLGTYKTQ EEAAVAYDMA AIEYRGVNAV TNFDISNYMD KIKKKNDQTQ QQQTEAQTET  240
VPNSSDSEEV EVEQQTTTIT TPPPSENLHM PPQQHQVQYT PHVSPREEES SSLITIMDHV  300
LEQDLPWSFM YTGLSQFQDP NLAFCKGDDD LVGMFDSAGF EEDIDFLFST QPGDETESDV  360
NNMSAVLDSV ECGDTNGAGG SMMHVDNKQK IVSFASSPSS TTTVSCDYAL DL        412

SEQ ID NO: 17          moltype = AA  length = 413
FEATURE                Location/Qualifiers
source                 1..413
                       mol_type = protein
                       organism = synthetic construct
SEQUENCE: 17
MKRPLTTSPS SSSSTSSSAC ILPTQSETPR PKRAKRAKKS SLRSDVKPQN PTSPASTRRS  60
SIYRGVTRHR RTGRYEAHLW DKSSWNSIQN KKGKQVYLGA YDSEEAAAHT YDLAALKYWG  120
PNTILNFPVE TYTKELEEMQ RCTKEEYLAS LRRQSSGFSR GVSKYRGVAR HHHNGRWEAR  180
IGRVFGNKYL YLGTYNTQEE AAAAYDMAAI EYRGANAVTN FDIGNYIDRL KKKGVFPFPV  240
SQANHQEAVL AETKQEVEAK EEPTEEVKQC VEKEEAKEEK TEKKQQQEVE EAVITCCIDS  300
SESNELAWDF CMMDSGFAPF LTDSNLSSEN PIEYPELFNE MGFEDNIDFM FEEGKQDCLS  360
LENLDCCDGV VVVGRESPTS LSSSPLSCLS TDSASSTTTT ATTVTSVSWN YSV       413

SEQ ID NO: 18          moltype = AA  length = 395
FEATURE                Location/Qualifiers
source                 1..395
                       mol_type = protein
                       organism = synthetic construct
```

```
SEQUENCE: 18
MERSQRQSPP PPSPSSSSSS VSADTVLVPP GKRRRAATAK AGAEPNKRIR KDPAAAAAGK  60
RSSVYRGVTR HRRTGRFEAH LWDKHCLAAL HNKKKGRQVY LGAYDSEEAA ARAYDLAALK  120
YWGPETLLNF PVEDYSSEMP EMEAVSREEY LASLRRRSSG FSRGVSKYRG VARHHHNGRW  180
EARIGRVFGN KYLYLGTFDT QEEAAKAYDL AAIEYRGVNA VTNFDISCYL DHPLFLAQLQ  240
QEPQVVPALN QEPQPDQSET GTTEQEPESS EAKTPDGSAE PDENAVPDDT AEPLSTVDDS  300
IEEGLWSPCM DYELDTMSRP NFGSSINLSE WFADADFDCN IGCLFDGCSA ADEGSKDGVG  360
LADFSLFEAG DVQLKDVLSD MEEGIQPPAM ISVCN                            395

SEQ ID NO: 19          moltype = AA  length = 393
FEATURE                Location/Qualifiers
source                 1..393
                       mol_type = protein
                       organism = synthetic construct
SEQUENCE: 19
MTMERSQPQH QQSPPSPSSS SSCVSADTVL VPPGKRRRRA ATAKANKRAR KDPSDPPPAA  60
GKRSSVYRGV TRHRRTGRFE AHLWDKHCLA ALHNKKKGRQ VYLGAYDGEE AAARAYDLAA  120
LKYWGPEALL NFPVEDYSSE MPEMEAASRE EYLASLRRRS SGFSRGVSKY RGVARHHHNG  180
RWEARIGRVL GNKYLYLGTF DTQEEAAKAY DLAAIEYRGA NAVTNFDISC YLDHPLFLAQ  240
LQQEQPQVVP ALDQEPQADQ REPETTAQEP VSSQAKTPAD DNAEPDDIAE PLITVDNSVE  300
ESLWSPCMDY ELDTMSRSNF GSSINLSEWF TDADFDSDLG CLFDGRSAVD GGSKGGVGVA  360
DFSLFEAGDG QLKDVLSDME EGIQPPTIIS VCN                              393

SEQ ID NO: 20          moltype = AA  length = 417
FEATURE                Location/Qualifiers
source                 1..417
                       mol_type = protein
                       organism = synthetic construct
SEQUENCE: 20
MKRSSASSCS SSSSSSSSPS SSSSSACSAS SSCLDSVSPP NHHQLRSENS KSKRIRKIQT  60
KQDKCQTTAT TTSPSGGGRR SSIYRGVTRH RRTGRFEAHL WDKSSWNNIQ NKKGRQVYLG  120
AYDNEEAAAH TYDLAALKYW GQDTTLNFLI ETYSKELEEM QKMSKEEYLA SLRRRSSGFS  180
RGVSKYRGVA RHHHNGRWEA RIGRVFGNKY LYLGTYNTQE EAAAAYDMAA IEYRGANAVT  240
NFDVSHYIDR LKKKGIPLDK ILPETLSKGS KESEEIERTS PLPLPSPPSP SITPLHEEIV  300
SPQLLETECP QHPPCMDTCT TIVMDPIEEH ELTWSFCLDS GLVPLPAPDL PLANGCELPD  360
LLDDTGFEDN IDLIFDACRF GNDANPADEN GKERLSSAST SPSCSTTLTS VSCNYSV     417

SEQ ID NO: 21          moltype = AA  length = 433
FEATURE                Location/Qualifiers
source                 1..433
                       mol_type = protein
                       organism = synthetic construct
SEQUENCE: 21
MKRRLTSTNS SSSSPSSSVS SSTTTSSPIQ SETPRPKRAN KRAKKPSPSD DKTTNPTSPA  60
STRRSSIYRG VTRHRRTGRF EAHLWDKSSW NSIQNKKGKQ VYLGAYDSEE AAAHTYDLAA  120
LKYWGPDTIL NFPAETYTKE LEEMQRVTKE EYLASLRRQS SGFSRGVSKY RGVARHHHNG  180
RWEARIGRVF GNKYLYLGTY NTQEEAAAAY DMAAIEYRGA NAVTNFDISN YIDRLKKKGV  240
FPFPVSQANH QEEAILAEAK QEIEAKEEPT EEVKQQCVEE PPQVQKEEKA EQQGEEVVGY  300
KEEEAAVVNC CIDSSAIMEM NRCSNDNELA WNFCMMDSGF TPFLTDQNLS NENPIEYPEL  360
FNELAFEENI DFMFEEGKNE CLGLGNLDCC EVVVGRESPT SSSSPLSCFS TDSASSTTTT  420
TATTTSVSCN YSV                                                    433

SEQ ID NO: 22          moltype = AA  length = 431
FEATURE                Location/Qualifiers
source                 1..431
                       mol_type = protein
                       organism = synthetic construct
SEQUENCE: 22
MKRRLTSTNS SSSSPSSSVS SSTTTSSPIQ SETPRPKRAN KRAKKPSPSG DKPNNPTSPA  60
STRRSSIYRG VTRHRRTGRF EAHLWDKSSW NSIQNKKGKQ VYLGAYDSEE AAAHTYDLAA  120
LKYWGPDTIL NFPAETYTKE LEEMQRVTKE EYLASLRRQS SGFSRGVSKY RGVARHHHNG  180
RWEARIGRVF GNKYLYLGTY NTQEEAAAAY DMAAIEYRGA NAVTNFDISN YIDRLKKKGV  240
YPFPVSQANH QEEAILAEAK QEIEAKEEPT EEVKQQYVEE PPQQVQKEEK AEQQGEEFVA  300
YKEEEAAVVN CCIDSSAIMG MNRCSDDNEL AWNFCMMDSG FAPFLTDQNL PNENPIEYPE  360
LFNELAFEEN IDFMFEEGKN EYLGLGNLDC CDVVVVGRES PTSSSSPLSC FSTDSASSST  420
TTTSVSCNYS V                                                      431

SEQ ID NO: 23          moltype = AA  length = 434
FEATURE                Location/Qualifiers
source                 1..434
                       mol_type = protein
                       organism = synthetic construct
SEQUENCE: 23
MKRRLTSTNS SSSSPSSSVS SSTTTSSPIQ SETPRPKRAN KRAKKPSPSD DKPNNPTSPA  60
STRRSSIYRG VTRHRRTGRF EAHLWDKSSW NSIQNKKGKQ VYLGAYDSEE AAAHTYDLAA  120
LKYWGPDTIL NFPAETYTKE LEEMQRVTKE EYLASLRRQS SGFSRGVSKY RGVARHHHNG  180
RWEARIGRVF GNKYLYLGTY NTQEEAAAAY DMAAIEYRGA NAVTNFDISN YIDRLKKKGV  240
FPFPVSQANH QEEAILAEAK QEIEAKEEPT EEVKQQCVEE PPQVQKEEKA EQQGEEFVGY  300
NKEEEATVVN CSIDSSAIME MNRCSDDNEL AWNFCMMDSG FAPFLTDQNL SNENPIEYPE  360
```

-continued

```
LFNELAFEEN IDFMFEEGKN ECLGLGNMDC CDVVVVGRES PTSSSSPLSC FSTDSASSTT  420
TATTTTSVSC NYSV                                                    434

SEQ ID NO: 24          moltype = AA  length = 420
FEATURE                Location/Qualifiers
source                 1..420
                       mol_type = protein
                       organism = synthetic construct
SEQUENCE: 24
MKRSPPQPSP SPSSSPASSS SSPSSSDSSS SIAIPRKRAR TAAAAAGGGK ARAAAAKRPK  60
KDGKDSGSSS NGGGGGGGKR SSIYRGVTRH RRTGRFEAHL WDKNCFTSLQ NKKKGRQVYL  120
GAYDTEEAAA RAYDLAALKY WGPETTLNFS ADDYGKERSE MEAVSREEYL AALRRRSSGF  180
SRGVSKYRGV ARHHHNGRWE ARIGRVLGNK YLYLGTFDTQ EEAARAYDLA AIQYRGANAV  240
TNFDISRYLD QPQLLEQLQQ QQGPQVVAAL QEEAQRDHQS DNAVQELNSG EAQTPGGIDE  300
PIAIGDSTED INTSLTVDDI IEESLWSPYE FDIMAGVNVS NSMNLSELFS DVAFEGNIGC  360
LFEECSGIDD CSSRHGAGLA AFGLFTEGDD KLKDVSEMEM EVNPQANDVS CPPKMITVCN  420

SEQ ID NO: 25          moltype = AA  length = 426
FEATURE                Location/Qualifiers
source                 1..426
                       mol_type = protein
                       organism = synthetic construct
SEQUENCE: 25
MKRSPASSCS SSTSSVGFEV HHPIEKRRPK HPRRNNLKSQ KCKQNQTTTG GRRSSIYRGV  60
TRHRRTGRFE AHLWDKSSWN NIQSKKGKQV YLGAYDTEES AARTYDLAAL KYWGKDATLN  120
FPIETYTKDL EEMDKVSREE YLASLRRQSS GFSRGISKYR GVARHHHNGR WEARIGRVCG  180
NKYLYLGTYK TQEEAAVAYD MAAIEYRGVN AVTNFDISNY MDKIKKKNDQ TLQQQQTEVQ  240
TETVPNSSDS EEAEVEQQHT TTITTPPPSE NLHMLPQEHQ VQYTHHVTPR DEESSSLVTI  300
MEHVLEQDLP WSFMYTGLSQ FQDPNLALSK GDDDLAGMFD GAGFEEDIDF LFSTQPGDHE  360
TESDVNNMSA VLDSVECGDT NGAGGRSMVY HHVDNNNKQK KMLSFASSSS PSSTTTTVSC  420
DYALDL                                                             426

SEQ ID NO: 26          moltype = AA  length = 412
FEATURE                Location/Qualifiers
source                 1..412
                       mol_type = protein
                       organism = synthetic construct
SEQUENCE: 26
MKRSPASSCS SSTSSVGFEA PIEKRRPKHP RRNNLKSQKC KQNQTTTGGR RSSIYRGVTR  60
HRRTGRFEAH LWDKSSWNNI QSKKGRQVYL GAYDTEESAA RTYDLAALKY WGKDATLNFP  120
IETYTKELEE MDKVSREEYL ASLRRQSSGF SRGLSKYRGV ARHHHNGRWE ARIGRVCGNK  180
YLYLGTYKTQ EEAAVAYDMA AIEYRGVNAV TNFDISNYMD KIKKKNDQTQ QQQTEAQTET  240
VPNSSDSEEV EVEQQTTTIT TPPPSENLHM PPQQHQVQYT PHVSPREEES SSLITIMDHV  300
LEQDLPWSFM YTGLSQFQDP NLAFCKGDDD LVGMFDSAGF EEDIDFLFST QPGDETESDV  360
NNMSAVLDSV ECGDTNGAGG SMMHVDNKQK IVSFASSPSS TTTVSCDYAL DL          412
```

ENGINEERED REGULATOR FOR IMPROVED PLANT OIL YIELD

CROSS REFERENCE TO RELATED APPLICATIONS

This application is a national stage application of PCT/SG2022/050683, filed Sep. 22, 2022, which claims priority to Singapore Application No. 10202250129P, filed Jun. 1, 2022, and Singapore Application No. 10202110937Q, filed Sep. 30, 2021, each of which are hereby incorporated by reference in their entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 33,303 Byte XML file named "Engineered Regulator for Improved Plant Oil Yield.xml," created on Mar. 26, 2024.

FIELD OF INVENTION

The invention relates generally to the field of molecular biology. Provided herein are isolated polynucleotides or polypeptides that lead to improved plant oil yields.

BACKGROUND

Edible plant oil obtained from seeds, pulps, fruits and plumules is primarily made up of triacylglycerols (TAGs, familiar to most people as vegetable oils) that comprises glycerol and fatty acids (FAs) linked by ester bonds. TAG can serve as the energy and carbon source to support seed germination and seedling development. Edible plant oils are essential for human diet and nutrition, and have been widely used in daily cooking, cosmetics and health supplements. In addition, plant oils have broad industrial applications, including serving as resource for biomaterials and fuels. Approximately 100 billion kilograms of plant oil, worth about US$120 billion, was produced in 2011. Global demand for vegetable oils is increasing rapidly. The rising demand of vegetable oils cannot be met by traditional production methods. Hence, there is a need to develop new methods for producing vegetable oils.

Accordingly, it is generally desirable to overcome or ameliorate one or more of the aforementioned difficulties.

SUMMARY

Disclosed herein is an isolated polynucleotide encoding a polypeptide that is distinguished from a wild-type Wrinkled1 polypeptide by at least one amino acid substitution in the wild-type Wrinkled1 amino acid sequence, wherein the at least one amino acid substitution comprises an amino acid substitution at a position corresponding to position 74 as set forth in SEQ ID NO: 1.

Disclosed herein is a polypeptide encoded by an isolated polynucleotide as defined herein.

Disclosed herein is a construct comprising an isolated polynucleotide as defined herein.

Disclosed herein is a vector comprising a construct as defined herein.

Disclosed herein is a method of preparing a transgenic plant cell, the method comprising transforming a plant cell with a construct as defined herein or a vector as defined herein.

Disclosed herein is a transgenic plant, plant cell or plant seed comprising a polynucleotide as defined herein or a construct as defined herein.

BRIEF DESCRIPTION OF DRAWINGS

Embodiments of the present invention are hereafter described, by way of non-limiting example only, with reference to the accompanying drawings in which.

DETAILED DESCRIPTION

Figure 1:
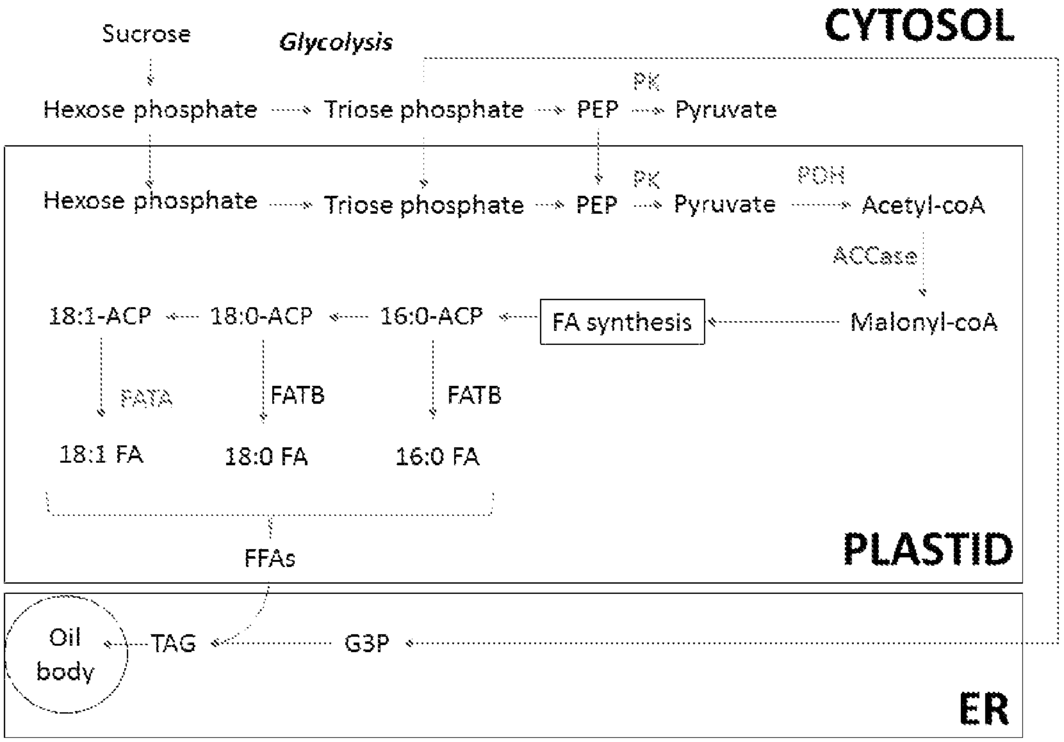
FIG. 1. Overview of TAG biosynthesis. FA synthesis starts in the plastids and assembly with G3P to TAG takes place in the ER. The enzymes PDH and FATA are upregulated in mutants overexpressing Wrinkled1 (WRI1), and enzymes, PK: PI-PKβ1; ACCase: BCCP2, are direct targets of WRI1.
Figure 2:
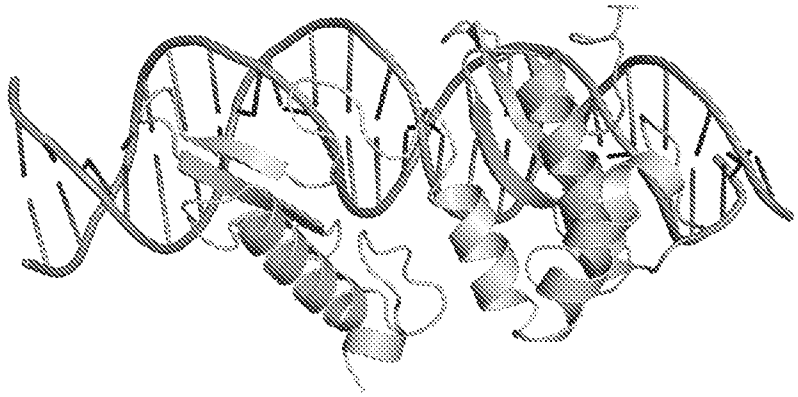
FIG. 2. Crystal structure of AtWRI1-DNA

The present specification teaches an isolated polynucleotide encoding a polypeptide that is distinguished from a wild-type Wrinkled1 (WRI1) polypeptide by at least one amino acid substitution in the wild-type WRI1 amino acid sequence.

The isolated polynucleotide may encode a polypeptide that is distinguished from a wild-type Wrinkled1 (WRI1) polypeptide by at least one amino acid substitution in the wild-type WRI1 amino acid sequence, wherein the at least one amino acid substitution is at a position corresponding to position 74 of the wild-type Wrinkled1 (WRI1) polypeptide.

Provided herein is an isolated polynucleotide encoding a polypeptide that is distinguished from a wild-type Wrinkled1 polypeptide by at least one amino acid substitution in the wild-type Wrinkled1 amino acid sequence, wherein the at least one amino acid substitution comprises an amino acid substitution at a position corresponding to position 74 as set forth in SEQ ID NO: 1.

WRI1 is a transcription factor that can increase the synthesis of proteins involved in oil synthesis. Modification of plants to express increased levels of stabilized WRI1 transcription factors can further increase the oil content of seeds and non-seed tissues (e.g., leaves, stalks and roots) in a variety of transgenic plants. Without being bound by theory, the inventors have engineered the WRI1 protein by one single residue mutation leading to higher affinity for its target DNA as well as oil production. Plants can be generated as described herein to include WRI1 nucleic acids that encode engineered WRI transcription factors. Plants are especially desirable when the WRI1 nucleic acids are operably linked to control sequences capable of WRI1 expression in a multitude of plant tissues, or in selected tissues and during selected parts of the plant life cycle to optimize the synthesis of oil. Such control sequences are typically heterologous to the coding region of the WRI1 nucleic acids.

The term "polynucleotide" or "nucleic acid" is used interchangeably herein to refer to a polymer of nucleotides, which can be mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

As used herein, "isolated" means a nucleic acid or polypeptide has been removed from its natural or native cell. Thus, the nucleic acid or polypeptide can be physically isolated from the cell, or the nucleic acid or polypeptide can be present or maintained in another cell where it is not naturally present or synthesized. The isolated nucleic acid or the isolated polypeptide can also be a nucleic acid or protein that is modified but has been introduced into a cell where it is or was naturally present. Thus, a modified isolated nucleic acid or an isolated polypeptide expressed from a modified isolated nucleic acid can be present in a cell along with a wild copy of the (unmodified) natural nucleic acid and along with wild type copies of the (natural) polypeptide.

As used with reference to polypeptides, the term "wild-type" refers to any polypeptide having an amino acid sequence present in a polypeptide from a naturally occurring organism, regardless of the source of the molecule; i.e., the term "wild-type" refers to sequence characteristics, regardless of whether the molecule is purified from a natural source; expressed recombinantly, followed by purification; or synthesized.

An "isolated polynucleotide" or "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

An isolated nucleic acid may be operably linked to one or more expression control sequences.

The term "encoding" or "encodes" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e. rRNA, tRNA and mRNA) or a defined sequence of amino acids and the biological properties resulting therefrom. Thus, a gene encodes a protein if transcription of a gene and translation of mRNA corresponding to that gene produces the protein in a cell or other biological system. Both the coding strand and the non-coding strand, used as the template for transcription of a gene or cDNA, can be referred to as encoding the protein or other product of that gene or cDNA.

The terms "polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylation, acetylation, phosphorylation and the like. Soluble forms of the subject proteinaceous molecules are particularly useful. Included within the definition are, for example, polypeptides containing one or more analogs of an amino acid including, for example, unnatural amino acids or polypeptides with substituted linkages.

The term "substitution" as used herein refers to the presence of an amino acid residue at a certain position of the derivative sequence which is different from the amino acid residue which is present or absent at the corresponding position in the reference sequence.

The term "at least one substitution" may refer to one, two, three, four, five, six, seven, eight, nine, ten or more substitutions.

The polypeptide as defined herein may, for example, have one or more "conservative amino acid substitution". A "conservative amino acid substitution" is one in which the amino acid residue is replaced with an amino acid residue having a similar side chain. Families of amino acid residues having similar side chains have been defined in the art, which can be generally sub-classified as follows:

AMINO ACID SUB-CLASSIFICATION

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G and I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The term "at least 70%" as used herein includes at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more.

The polypeptide as referred to herein may be distinguished from the WRI1 polypeptide by at least one amino acid substitution in the AP2 region of the wild-type WRI1 amino acid sequence.

In one embodiment, the wild-type WRI1 polypeptide has an amino acid sequence having at least 70% (or 80%, 90%, 95% or 99%) sequence identity to SEQ ID NO: 1 or a fragment thereof.

In one embodiment, the wild-type WRI1 polypeptide has an amino acid sequence having at least 70% (or 80%, 90%, 95% or 99%) sequence identity to the AP2 region (positions 55-255) of SEQ ID NO: 1.

Related WRI1 sequences can be isolated from a variety of plant types such as alfalfa (e.g., forage legume alfalfa), algae, avocado, barley, broccoli, Brussels sprouts, cabbage, canola, cassava, cauliflower, cole vegetables, collards, crucifers, grain legumes, grasses (e.g., forage grasses), jatropa, kale, kohlrabi, maize, miscanthus, mustards, nut sedge, oats, oil firewood trees, oilseeds, potato, radish, rapeseed, rice, rutabaga, sorghum, sugar beets, sugarcane, sunflower, switchgrass, tobacco, tomato, turnips, and wheat The wild-type WRI1 polypeptide may, for example, be from *Arabidopsis thaliana, Brassica napus, Glycine max, Elaeis guineensis, Zea mays* or *Camelina sativa.*

The wild-type WRI1 polypeptide may be from *Arabidopsis thaliana, Brachypodium distachyon, Brassica napus, Camelina sativa, Glycine max, Elaeis guineensis, Jatropha curcas* or *Zea mays.*

In one embodiment, the wild-type WRI1 polypeptide has an amino acid sequence having at least 70% (or 80%, 90%, 95% or 99%) sequence identity to SEQ ID NO: 7 or a fragment thereof.

In one embodiment, the wild-type WRI1 polypeptide has an amino acid sequence having at least 70% (or 80%, 90%, 95% or 99%) sequence identity to SEQ ID NO: 8 or a fragment thereof.

In one embodiment, the wild-type WRI1 polypeptide has an amino acid sequence having at least 70% (or 80%, 90%, 95% or 99%) sequence identity to SEQ ID NO: 9 or a fragment thereof.

In one embodiment, the wild-type WRI1 polypeptide has an amino acid sequence having at least 70% (or 80%, 90%, 95% or 99%) sequence identity to SEQ ID NO: 10 or a fragment thereof.

In one embodiment, the wild-type WRI1 polypeptide has an amino acid sequence having at least 70% (or 80%, 90%, 95% or 99%) sequence identity to SEQ ID NO: 11 or a fragment thereof.

In one embodiment, the wild-type WRI1 polypeptide has an amino acid sequence having at least 70% (or 80%, 90%, 95% or 99%) sequence identity to SEQ ID NO: 12 or a fragment thereof.

In one embodiment, the wild-type WRI1 polypeptide has an amino acid sequence having at least 70% (or 80%, 90%, 95% or 99%) sequence identity to SEQ ID NO: 13 or a fragment thereof.

In one embodiment, the wild-type WRI1 polypeptide has an amino acid sequence having at least 70% (or 80%, 90%, 95% or 99%) sequence identity to SEQ ID NO: 14 or a fragment thereof.

In one embodiment, the wild-type WRI1 polypeptide has an amino acid sequence having at least 70% (or 80%, 90%, 95% or 99%) sequence identity to SEQ ID NO: 15 or a fragment thereof.

In one embodiment, the wild-type WRI1 polypeptide has an amino acid sequence having at least 70% (or 80%, 90%, 95% or 99%) sequence identity to SEQ ID NO: 16 or a fragment thereof.

In one embodiment, the at least one amino acid substitution is at a position corresponding to position 74 of the wild-type Wrinkled1 (WRI1) polypeptide. The at least one amino acid substitution may comprise an amino acid substitution at a position corresponding to position 74 as set forth in SEQ ID NO: 1. The amino acid substitution corresponding to position 74 may, for example, be a substitution to a positively charged residue. The positively charged residue may be arginine or lysine.

In one embodiment, the polypeptide is distinguished from a wild-type Wrinkled1 (WRI1) polypeptide by at least one amino acid substitution in the wild-type WRI1 amino acid sequence, wherein the wild-type WRI1 amino acid sequence is an amino acid sequence having at least 70% (or 80%, 90%, 95% or 99%) sequence identity to SEQ ID NO: 1, 7, 8, 9, 10, 11, 12, 13, 14, 15 or 16 or a fragment thereof. The at least one amino acid substitution may comprise an amino acid substitution at a position corresponding to position 74 as set forth in SEQ ID NO: 1.

The polypeptide may have an amino acid sequence having at least 70% (or 80%, 90%, 95% or 99%) sequence identity to any one of SEQ ID NO: 2 or SEQ ID NO: 17-26, or a fragment thereof.

Provided herein is an isolated polynucleotide encoding a polypeptide that is distinguished from a wild-type Wrinkled1 polypeptide by at least one amino acid substitution in the wild-type Wrinkled1 amino acid sequence, wherein the wild-type Wrinkled1 amino acid sequence has an amino acid sequence having at least 70% sequence identity to SEQ ID NO: 7, and wherein the at least one amino acid substitution comprises an amino acid substitution at a position corresponding to position 71 as set forth in SEQ ID NO: 7.

Provided herein is an isolated polynucleotide encoding a polypeptide that is distinguished from a wild-type Wrinkled1 polypeptide by at least one amino acid substitution in the wild-type Wrinkled1 amino acid sequence, wherein the wild-type Wrinkled1 amino acid sequence has an amino acid sequence having at least 70% sequence identity to SEQ ID NO: 8, and wherein the at least one amino acid substitution comprises an amino acid substitution at a position corresponding to position 73 as set forth in SEQ ID NO: 8.

Provided herein is an isolated polynucleotide encoding a polypeptide that is distinguished from a wild-type Wrinkled1 polypeptide by at least one amino acid substitution in the wild-type Wrinkled1 amino acid sequence, wherein the wild-type Wrinkled1 amino acid sequence has an amino acid sequence having at least 70% sequence identity to SEQ ID NO: 9, and wherein the at least one amino acid substitution comprises an amino acid substitution at a position corresponding to position 75 as set forth in SEQ ID NO: 9.

Provided herein is an isolated polynucleotide encoding a polypeptide that is distinguished from a wild-type Wrinkled1 polypeptide by at least one amino acid substitution in the wild-type Wrinkled1 amino acid sequence, wherein the wild-type Wrinkled1 amino acid sequence has an amino acid sequence having at least 70% sequence identity to SEQ ID NO: 10, and wherein the at least one amino acid substitution comprises an amino acid substitution at a position corresponding to position 92 as set forth in SEQ ID NO: 10.

Provided herein is an isolated polynucleotide encoding a polypeptide that is distinguished from a wild-type Wrinkled1 polypeptide by at least one amino acid substitution in the wild-type Wrinkled1 amino acid sequence, wherein the wild-type Wrinkled1 amino acid sequence has an amino acid sequence having at least 70% sequence identity to SEQ ID NO: 11, 12 or 13, and wherein the at least one amino acid substitution comprises an amino acid substitution at a position corresponding to position 76 as set forth in SEQ ID NO: 11, 12 or 13.

Provided herein is an isolated polynucleotide encoding a polypeptide that is distinguished from a wild-type Wrinkled1 polypeptide by at least one amino acid substitution in the wild-type Wrinkled1 amino acid sequence, wherein the wild-type Wrinkled1 amino acid sequence has an amino acid sequence having at least 70% sequence identity to SEQ ID NO: 14, and wherein the at least one amino acid substitution comprises an amino acid substitution at a position corresponding to position 92 as set forth in SEQ ID NO: 14.

Provided herein is an isolated polynucleotide encoding a polypeptide that is distinguished from a wild-type Wrinkled1 polypeptide by at least one amino acid substitution in the wild-type Wrinkled1 amino acid sequence, wherein the wild-type Wrinkled1 amino acid sequence has an amino acid sequence having at least 70% sequence identity to SEQ ID NO: 15, and wherein the at least one amino acid substitution comprises an amino acid substitution at a position corresponding to position 65 as set forth in SEQ ID NO: 15.

Provided herein is an isolated polynucleotide encoding a polypeptide that is distinguished from a wild-type Wrinkled1 polypeptide by at least one amino acid substitution in the wild-type Wrinkled1 amino acid sequence, wherein the wild-type Wrinkled1 amino acid sequence has an amino acid sequence having at least 70% sequence identity to SEQ ID NO: 16, and wherein the at least one amino acid substitution comprises an amino acid substitution at a position corresponding to position 63 as set forth in SEQ ID NO: 16.

Disclosed herein is an isolated polynucleotide encoding a polypeptide comprising a positively charged amino acid residue at position 74 corresponding to a wild-type Wrinkled1 (WRI1) polypeptide (such as SEQ ID NO: 1).

Provided herein is an isolated polynucleotide encoding a polypeptide comprising a positively charged amino acid residue at a position corresponding to position 74 as set forth in SEQ ID NO: 1.

The at least one amino acid substitution may further comprise an amino acid substitution at a position corresponding to position 90 as set forth in SEQ ID NO: 1. The amino acid substitution at position 90 may be an amino acid substitution to a glutamic or aspartic acid.

The at least one amino acid substitution may further comprise an amino acid substitution at a position corresponding to position 91 as set forth in SEQ ID NO: 1. The amino acid substitution at position 91 may be an amino acid substitution to glycine.

The at least one amino acid substitution may further comprise an amino acid substitution at a position corresponding to position 92 as set forth in SEQ ID NO: 1. The amino acid substitution at position 92 may be an amino acid substitution to a positively charged amino acid residue such as lysine or arginine.

The at least one amino acid substitution may further comprise an amino acid substitution at a position corresponding to position 174 as set forth in SEQ ID NO: 1. The amino acid substitution at position 174 may be an amino acid substitution to a glutamine.

The at least one amino acid substitution may further comprise an amino acid substitution at a position corresponding to position 175 as set forth in SEQ ID NO: 1. The amino acid substitution at position 175 may be an amino acid substitution to a glutamine.

The at least one amino acid substitution may further comprise an amino acid substitution at a position corresponding to position 176 as set forth in SEQ ID NO: 1. The amino acid substitution at position 176 may be an amino acid substitution to a lysine.

Provided herein is an isolated polynucleotide encoding a polypeptide that is distinguished from a wild-type Wrinkled1 polypeptide by at least one amino acid substitution in the wild-type Wrinkled1 amino acid sequence, wherein the at least one amino acid substitution comprises an amino acid substitution at a position corresponding to positions 74, 90, 91, 92, 174, 175 and 176 as set forth in SEQ ID NO: 1.

The at least one amino acid substitution may comprise amino acid substitutions at positions 74, 90, 91 and 92 as set forth in SEQ ID NO: 1.

The at least one amino acid substitution may comprise amino acid substitutions at positions 74, 174, 175 and 176 as set forth in SEQ ID NO: 1.

Disclosed herein is a polypeptide encoded by an isolated polynucleotide as defined herein.

In order to engineer plants with increased vegetable oil content that, one of skill in the art can introduce nucleic acids encoding the WRI1 proteins described herein into the plants to promote the production of oils.

For example, one of skill in the art can generate genetically-modified plants that contain nucleic acids encoding WRI1 proteins within their somatic and/or germ cells. Such genetic modification can be accomplished by procedures available in the art. For example, one of skill in the art can prepare an expression cassette or expression vector that can express one or more encoded WRI1 proteins. Plant cells can be transformed by the expression cassette or expression vector, and whole plants (and their seeds) can be generated from the plant cells that were successfully transformed with the WRI1 nucleic acids. Some procedures for making such genetically modified plants and their seeds are described below.

Disclosed herein is a construct comprising an isolated polynucleotide as defined herein.

The term "construct" refers to a recombinant genetic molecule including one or more isolated nucleic acid sequences from different sources. Thus, constructs are chimeric molecules in which two or more nucleic acid sequences of different origin are assembled into a single nucleic acid molecule and include any construct that contains (1) nucleic acid sequences, including regulatory and coding sequences that are not found together in nature (i.e., at least one of the nucleotide sequences is heterologous with respect to at least one of its other nucleotide sequences), or (2) sequences encoding parts of functional RNA molecules or proteins not naturally adjoined, or (3) parts of promoters that are not naturally adjoined. Representative constructs include any recombinant nucleic acid molecule such as a plasmid, cosmid, virus, autonomously replicating polynucleotide molecule, phage, or linear or circular single stranded or double stranded DNA or RNA nucleic acid molecule, derived from any source, capable of genomic integration or autonomous replication, comprising a nucleic acid molecule where one or more nucleic acid molecules have been operably linked. Constructs of the present invention will generally include the necessary elements to direct expression of a nucleic acid sequence of interest that is also contained in the construct, such as, for example, a target nucleic acid sequence or a modulator nucleic acid sequence. Such elements may include control elements such as a promoter that is operably linked to (so as to direct transcription of) the nucleic acid sequence of interest, and often includes a polyadenylation sequence as well. Within certain embodiments of the invention, the construct may be contained within a vector. In addition to the components of the construct, the vector may include, for example, one or more selectable markers, one or more origins of replication, such as prokaryotic and eukaryotic origins, at least one multiple cloning site, and/or elements to facilitate stable integration of the construct into the genome of a host cell. Two or more constructs can be contained within a single nucleic acid molecule, such as a single vector, or can be containing within two or more separate nucleic acid molecules, such as two or more separate vectors.

An "expression construct" generally includes at least a control sequence operably linked to a nucleotide sequence of interest. In this manner, for example, promoters in operable connection with the nucleotide sequences to be expressed are provided in expression constructs for expression in an organism or part thereof including a host cell. For the practice of the present invention, conventional compositions, and methods for preparing and using constructs and host cells are well known to one skilled in the art, see for example, Molecular Cloning: A Laboratory Manual, 3rd edition Volumes 1, 2, and 3. J. F. Sambrook, D. W. Russell, and N. Irwin, Cold Spring Harbor Laboratory Press, 2000.

The isolated polynucleotide may be operably linked to a control element.

By "control element" or "control sequence" is meant nucleic acid sequences (e.g., DNA) necessary for expression of an operably linked coding sequence in a particular host cell. The control sequences that are suitable for prokaryotic cells for example, include a promoter, and optionally a cis-acting sequence such as an operator sequence and a ribosome binding site. Control sequences that are suitable for eukaryotic cells include transcriptional control sequences such as promoters, polyadenylation signals, transcriptional enhancers, translational control sequences such as translational enhancers and internal ribosome binding sites (IRES), nucleic acid sequences that modulate mRNA stability, as well as targeting sequences that target a product encoded by a transcribed polynucleotide to an intracellular compartment within a cell or to the extracellular environment.

The WRI1 nucleic acids can be operably linked to a promoter, which provides for expression of an mRNA expressed from the WRI1 nucleic acids. The promoter can be a promoter functional in plants and/or seeds, and/or it can be a promoter functional during plant growth and development or in a mature plant. The promoter can be a heterologous promoter. As used herein, "heterologous" when used in reference to a gene or nucleic acid refers to a gene or nucleic acid that has been manipulated in some way. For example, a heterologous promoter is a promoter that contains sequences that are not naturally linked to an associated coding region.

A WRI1 nucleic acid is operably linked to the promoter when it is located downstream from the promoter, thereby forming a key portion of an expression cassette. Any of the nucleic acids encoding WRI1 proteins can have an ATG start codon, either naturally or as an added codon, for example between the promoter and the 5' end of the WRI1 coding region.

Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides a very low level of gene expression. An inducible promoter is a promoter that provides for the turning on and off gene expression in response to an exogenously added agent, or to an environmental or developmental stimulus. For example, a bacterial promoter such as the Ptac promoter can be induced to vary levels of gene expression depending on the level of isothiopropylgalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired. In some embodiments, the promoter is an inducible promoter and/or a tissue-specific promoter.

Examples of promoters that can be used include, but are not limited to, the CaMV 35S promoter, or others such as CaMV 19S, nos, Adh1, sucrose synthase, α-tubulin, ubiquitin, actin, cab, PEPCase, the CCR (cinnamoyl CoA:NADP oxidoreductase, EC 1.2.1.44) promoter sequence isolated from *Lollium perenne*, (or a perennial ryegrass) and/or those associated with the R gene complex. Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene and the actin promoter from rice. Seed specific promoters, such as the phaseolin promoter from beans, may also be used. Other promoters useful in the practice of the invention are known to those of skill in the art.

Alternatively, novel tissue specific promoter sequences may be employed in the practice of the present invention. cDNA clones from a particular tissue are isolated and those clones which are expressed specifically in that tissue are identified, for example, using Northern blotting. Preferably, the gene isolated is not present in a high copy number but is relatively abundant in specific tissues. The promoter and control elements of corresponding genomic clones can then be localized using techniques well known to those of skill in the art.

For example, the promoter can be an inducible promoter. Such inducible promoters can be activated by agents such as chemicals, hormones, sugars, metabolites, or by the age or developmental stage of the plant. For example, the promoter can be an ethanol-inducible promoter, a sugar-inducible promoter, a senescence-induced promoter or any promoter activated in vegetative tissues of dicots and monocots. One example of a sugar-inducible promoter is a patatin B33 promoter. Such a patatin B33 promoter can, for example, be used in tuber crops such as cassava, potato, rutabaga, sugar beet, and the like.

Disclosed herein is a vector comprising a construct as defined herein.

By the term "vector", as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of a nucleic acid that encodes a polypeptide of the present invention to the patient, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94: 12744-12746). Examples of viral vectors include, but are not limited to, a lentiviral vector, a recombinant adenovirus, a recombinant retrovirus, a recombinant adeno-associated virus, a recombinant avian pox virus, and the like. Examples of non-viral vectors include, but are not limited to, liposomes, polyamine derivatives of DNA, and the like.

Disclosed herein is a method of preparing a transgenic plant cell, the method comprising transforming a plant cell with a construct as defined herein or a vector as defined herein.

Disclosed herein is a transgenic plant, plant cell or plant seed comprising a polynucleotide as defined herein or a construct as defined herein.

In one embodiment, there is provided a transgenic plant comprising a polynucleotide as defined herein or a construct as defined herein.

In one embodiment, there is provided a transgenic plant cell comprising a polynucleotide as defined herein or a construct as defined herein.

In one embodiment, there is provided a transgenic plant seed comprising a polynucleotide as defined herein or a construct as defined herein.

The term "transgenic" when used in reference to a plant or leaf or vegetative tissue or seed for example a "transgenic plant," transgenic leaf," "transgenic vegetative tissue," "transgenic seed," or a "transgenic host cell" refers to a plant or leaf or tissue or seed that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

As used herein, the term "plant" is used in its broadest sense. It includes, but is not limited to, any species of grass (e.g. turf grass), ornamental or decorative, crop or cereal, fodder or forage, fruit or vegetable, fruit plant or vegetable plant, herb plant, woody plant, flower plant or tree. It is not meant to limit a plant to any particular structure. It also refers to a unicellular plant (e.g. microalga) and a plurality of plant cells that are largely differentiated into a colony (e.g. volvox) or a structure that is present at any stage of a plant's development. Such structures include, but are not limited to, a seed, a tiller, a sprig, a stolen, a plug, a rhizome, a shoot, a stem, a leaf, a flower petal, a fruit, et cetera.

The term "plant tissue" includes differentiated and undifferentiated tissues of plants including those present in roots, shoots, leaves, pollen, seeds, and tumors, as well as cells in culture (e.g., single cells, protoplasts, embryos, callus, etc.). Plant tissue may be in planta, in organ culture, tissue culture, or cell culture.

As used herein, the term "plant part" as used herein refers to a plant structure or a plant tissue, for example, pollen, an ovule, a tissue, a pod, a seed, a leaf and a cell. Plant parts may comprise one or more of a tiller, plug, rhizome, sprig, stolen, meristem, crown, and the like. In some instances, the plant part can include vegetative tissues of the plant.

Vegetative tissues or vegetative plant parts do not include plant seeds, and instead include non-seed tissues or parts of a plant. The vegetative tissues can include reproductive tissues of a plant, but not the mature seeds.

The term "seed" refers to a ripened ovule, consisting of the embryo and a casing.

The term "propagation" refers to the process of producing new plants, either by vegetative means involving the rooting or grafting of pieces of a plant, or by sowing seeds. The terms "vegetative propagation" and "asexual reproduction" refer to the ability of plants to reproduce without sexual reproduction, by producing new plants from existing vegetative structures that are clones, i.e., plants that are identical in all attributes to the mother plant and to one another. For example, the division of a clump, rooting of proliferations, or cutting of mature crowns can produce a new plant.

The term "heterologous" when used in reference to a nucleic acid refers to a nucleic acid that has been manipulated in some way. For example, a heterologous nucleic acid includes a nucleic acid from one species introduced into another species. A heterologous nucleic acid also includes a nucleic acid native to an organism that has been altered in some way (e.g., mutated, added in multiple copies, linked to a non-native promoter or enhancer sequence, etc.). Heterologous nucleic acids can include cDNA forms of a nucleic acid; the cDNA may be expressed in either a sense (to produce mRNA) or anti-sense orientation (to produce an anti-sense RNA transcript that is complementary to the mRNA transcript). For example, heterologous nucleic acids can be distinguished from endogenous plant nucleic acids in that the heterologous nucleic acids are typically joined to nucleic acids comprising regulatory elements such as promoters that are not found naturally associated with the natural gene for the protein encoded by the heterologous gene. Heterologous nucleic acids can also be distinguished from endogenous plant nucleic acids in that the heterologous nucleic acids are in an unnatural chromosomal location, or are associated with portions of the chromosome not found in nature (e.g., the heterologous nucleic acids are expressed in tissues where the gene is not normally expressed).

The WRI1 nucleic acid can be introduced into a recipient cell to create a transformed cell by available methods. The frequency of occurrence of cells taking up exogenous (foreign) DNA can be low, and it is likely that not all recipient cells receiving DNA segments or sequences will result in a transformed cell wherein the DNA is stably integrated into the plant genome and/or expressed. Some may show only initial and transient gene expression. However, cells from virtually any dicot or monocot species can be stably transformed, and those cells can be regenerated into transgenic plants, for example, through the application of the techniques disclosed herein.

Another aspect of the invention is a plant species with increased vegetative tissue oil content, wherein the plant has an introduced WRI1 nucleic acid. The plant can be a monocotyledon or a dicotyledon. Another aspect of the invention includes plant cells (e.g., embryonic cells or other cell lines) that can regenerate fertile transgenic plants. Another aspect of the invention includes transgenic seeds from which transgenic plants can be grown. The plants, cells and seeds can be either monocotyledons or dicotyledons. The cell(s) may be in a suspension cell culture or may be in an intact plant part, such as an immature embryo, or in a specialized plant tissue, such as callus, such as Type I or Type II callus.

Examples of plants, seeds, and/or plant cells that can be modified as described herein to express the WRI1 transcription factors proteins include alfalfa (e.g., forage legume alfalfa), algae, avocado, barley, broccoli, Brussels sprouts, cabbage, canola, cassava, cauliflower, cole vegetables, collards, corn, crucifers, grain legumes, grasses (e.g., forage grasses), jatropa, kale, kohlrabi, maize, *miscanthus*, mustards, nut sedge, oats, oil firewood trees, oilseeds, potato, radish, rape, rapeseed, rice, rutabaga, sorghum, soybean, sugar beets, sugarcane, sunflower, switchgrass, tobacco, tomato, turnips, and wheat. In some embodiments, the plant is a Brassicaceae or other Solanaceae species.

Transformation of the cells of the plant tissue source can be conducted by any one of a number of methods known to those of skill in the art. Examples are: Transformation by direct DNA transfer into plant cells by electroporation; direct DNA transfer to plant cells by PEG precipitation; direct DNA transfer to plant cells by microprojectile bombardment and DNA transfer to plant cells via infection with Agrobacterium. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol. Monocots such as *Zea mays* can be transformed via microprojectile bombardment of embryogenic callus tissue or immature embryos, or by electroporation following partial enzymatic degradation of the cell wall with a pectinase-containing enzyme. For example, embryogenic cell lines derived from immature *Zea mays* embryos can be transformed by accelerated particle treatment. Excised immature embryos can also be used as the target for transformation prior to tissue culture induction, selection and regeneration. Furthermore, methods for transformation of monocotyledonous plants utilizing *Agrobacterium tumefaciens* have been previously described.

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but lack functions for disease induction.

Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

After effecting delivery of one or more WRI1 nucleic acid(s) to recipient cells by any of the methods discussed above (e.g., in an expression vector), the transformed cells can be identified for further culturing and plant regeneration. In order to improve the ability to identify transformants, one may desire to employ a selectable or screenable marker gene as, or in addition to, the WRI1 nucleic acids. In this case, one would then generally assay the potentially transformed cell population by exposing the cells to a selective agent or agents, or one would screen the cells for the desired marker gene trait. Alternatively, the introduced (e.g., transgenic) nucleic acids can be detected and/or characterized by use of a nucleic acid probe to detect the presence of an expression cassette and/or expressed RNA. The introduced nucleic acids can also be detected and/or evaluated by sequencing.

Regeneration and Seed Production:

Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened. Plants can be matured either in a growth chamber or greenhouse. Plants are regenerated from about 6 weeks to 10 months after a transformant is identified, depending on the initial tissue. During regeneration, cells are grown on solid media in tissue culture vessels. After the regenerating plants have reached the stage of shoot and root development, they may be transferred to a greenhouse for further growth and testing.

Mature plants are then obtained from cell lines that express the desired trait(s). In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the WRI1 nucleic acid into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced WRI1 nucleic acid, the plant is self-pollinated at least once in order to produce a homozygous backcross converted inbred containing the WRI1 nucleic acid. Progeny of these plants are true breeding.

Alternatively, seed from transformed plants regenerated from transformed tissue cultures is grown in the field and self-pollinated to generate true breeding plants.

Seed from the fertile transgenic plants can be evaluated for the presence and/or expression of the WRI1 nucleic acid (or the WRI1 protein product). Transgenic plant and/or seed tissue can be analyzed for WRI1 expression using standard methods such as SDS polyacrylamide gel electrophoresis, liquid chromatography (e.g., HPLC) or other means of detecting a WRI1 protein.

Once a transgenic seed expressing the WRINKLED transcription factor and having an increase in oil in the plant tissue is identified, the seed can be used to develop true breeding plants. The true breeding plants are used to develop a line of plants with an increase in the percent of oil in the plant tissues while still maintaining other desirable functional agronomic traits. Adding the trait of increased oil/decreased carbohydrate production to the plant can be accomplished by back-crossing with this trait and with plants that do not exhibit these traits and studying the pattern of inheritance in segregating generations.

Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of an increased percent of oil in the plant. The resulting progeny are then crossed back to the parent that expresses the increased oil/decreased carbohydrate trait. The progeny from this cross will also segregate so that some of the progeny carry the traits and some do not. This back-crossing is repeated until an inbred line with the desirable functional agronomic traits, and with expression of the trait involving an increase in oil and/or a decrease in carbohydrate in the vegetative tissues of the plant. Such expression of the increased percentage of oil or decreased percentage of carbohydrate in plant tissues can be expressed in a dominant fashion.

Subsequent to back-crossing, the new transgenic plants can be evaluated for an increase in the weight percent of oil (TAG) incorporated into vegetative tissues of the plant. This can be done, for example, by thin layer chromatography (TLC), gas chromatography, gas chromatography-flame ionization detector (GC-FID), electrospray ionization mass spectrometry (ESI-MS), mass spectroscopy, nuclear magnetic resonance (NMR), high pressure liquid chromatography (HPLC), and/or infrared spectral analysis of plant tissue or by other available methods of detecting and quantifying oils in harvested plant tissues. The new transgenic plants can also be evaluated for a battery of functional agronomic characteristics such as lodging, kernel hardness, yield, resistance to disease, resistance to insect pests, drought resistance, and/or herbicide resistance.

Plants that can be generated by these methods include but are not limited to oil and/or starch plants (canola, potatoes, cassava, lupins, rape, rapeseed, soybean, sunflower and cottonseed), forage plants (alfalfa, clover and fescue), grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and eucalyptus). Examples of plants and/or plant cells that can be modified as described herein include alfalfa (e.g., forage legume alfalfa), algae, avocado, barley, broccoli, Brussels sprouts, cabbage, canola, cassava, cauliflower, cole vegetables, collards, corn, crucifers, grain legumes, grasses (e.g., forage grasses), jatropa, kale, kohlrabi, maize, miscanthus, mustards, nut sedge, oats, oil firewood trees, oilseeds, potato, radish, rape, rapeseed, rice, rutabaga, sorghum, soybean, sugar beets, sugarcane, sunflower, switchgrass, tobacco, tomato, turnips, and wheat.

To confirm the presence of the WRI1 nucleic acid in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant. In some embodiments, the amount of oil in plant tissues is quantified. Such a quantified oil content can be compared to a control plant, for example, a control plant of the same species that has not be modified to express the WRI1 transcription factor protein.

Provided herein is a method of generating oil comprising isolating plant tissue, cell, or seed as defined herein and extracting oil from the plant tissue, cell, or seed.

As used herein, "and/or" refers to and encompasses any and all possible combinations of one or more of the associated listed items, as well as the lack of combinations when interpreted in the alternative (or).

As used in this application, the singular form "a," "an," and "the" include plural references unless the context clearly dictates otherwise. For example, the term "an agent" includes a plurality of agents, including mixtures thereof.

Throughout this specification and the statements which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

EXAMPLES

Materials and Methods

Plasmid Construction

The coding region of AtWRI1$^{58-307}$ was codon optimized, synthesized and subcloned into pOPT370 MBP vector encoding Hexahistidine-Maltose binding protein (MBP) tag. The mutagenesis was finished by site-directed mutagenesis kit (New England Biolabs). All the insertions and mutagenesis were confirmed by DNA sequencing. For plant expression constructs, the coding sequence (CDS) of WRI1s (native form and variants) was amplified by PCR and cloned into pENTR4 (Thermo Fisher) or synthesized to pTwist ENTR by Twist Bioscience to obtain entry constructs. WRI1s entry constructs were introduced to pEarleyGate binary vectors (pEarleyGate100) by LR Clonase II (Thermo Fisher). To obtain proAtWRI1:AtWRI1 construct, CaMV 35S promoter was replaced by proAtWRI1 (2 kb upstream of the start codon).

Protein Expression and Purification

The plasmid encoding AtWRI1$^{58-307}$ was transformed into *E. coli* BL21 (DE3). A single colony was picked and inoculated into 10 mL 2×YT medium (16 g/L tryptone, 10 g/L yeast extract, and 5 g/L NaCl) supplemented with a final concentration of 100 μg/mL ampicillin for overnight growth at 37° C. The bacteria were then inoculated into 1 litter 2×YT medium and grown until OD600 reached ~0.6, the cells were then cooled down at cold room for one hour before adding the final concentration of 0.2 mM IPTG for protein expression at 16° C. overnight. The bacteria were harvested by centrifugation (Beckman Coulter Avanti-26, JA8.1, 4,000 rpm) for 10 minutes at 4° C., then resuspended in lysis buffer (25 mM Tris pH 7.5, 150 mM NaCl). Cells were lysed by sonication then crude lysate clarified by centrifugation (Beckman Coulter Avanti-26, JA25.5, 20,000 rpm,) for 1 hour at 4° C. The supernatant was incubated with 5 mL Nickel-NTA beads (Biobasic, Singapore) for 1 hour at 4° C. Then the beads were collected by centrifugation, washed by Buffer-A (25 mM Tris pH 7.5, 150 mM NaCl, 30 mM Imidazole. The protein was eluted by Buffer-B (25 mM Tris pH 7.5, 150 mM NaCl, 200 mM Imidazole). The eluted protein was incubated with Tobacco Etch Virus (TEV) protease to cut off the Hexahistidine-MBP tag for overnight at 4° C. The cut protein was separated by anion ion exchange, collected, concentrated, and loaded to size-exclusion chromatography using Hiload Superdex 200 16/60 pre-equilibrated with buffer (25 mM Tris pH 7.5, 150 mM NaCl). The fractions eluted from size-exclusion chromatography were collected, concentrated to 20 mg/mL and snap frozen, stored at −80° C. for future use. The selenomethionine (Se-Met) substituted WRI1 and the WRI1 mutants were purified similarly.

Analytical Gel Filtration Chromatography

Analytical gel filtration chromatography was performed using Superdex 200 Increase 10/300 GL (GE Healthcare) in buffer (25 mM Tris pH 7.5, 150 mM NaCl) for the following samples: WRI1, WRI1 and dsDNA in 1:1 ratio and dsDNA. WRI1 and its binding dsDNA were mixed and incubated on ice for 1 hour prior to loading.

Isothermal Titration Calorimetry (ITC) Measurement

ITC measurement was performed using MicroCal PEAQ-ITC (Malvern Instruments) at 20° C. 200 μM WRI1 binding ds-DNA (5'-TACTTCCTCGGTTTCATCGTCCAC (SEQ ID NO: 5)) was injected into the sample cell containing 20 μM WRI1 or its mutants in a total of 19 injections. Injection time was 4 s, with each 2 μL injection spaced across 150 s intervals. A titration of DNA to the buffer was performed using the same procedures. The raw data were processed and analyzed using MicroCal PEAQ-ITC analysis software.

Crystallization and Structure Determination

WRI1 (7.5 mg/mL) was mixed with equimolar WRI1 binding ds-DNA BCCP2(−34/−11) (5'-TACTTCCTCGGTTTCATCGTCCAC (SEQ ID NO: 5) and incubated at 4° C. for 1 hour. Crystallization screening was performed with Crystal Screen™ (CS), Index, PEG Rx and PEG/Ion Screen (Hampton Research) using the sitting drop vapor diffusion method at 20° C. on Intelli-Plate 96-3 LVR (Art Robbins Instruments). Crystal appeared in crystal screening A9 condition (0.2 M Ammonium acetate, 0.1 M Sodium citrate tribasic dihydrate pH 5.6, 30% w/v Polyethylene glycol 4,000). The final optimized condition for crystal growth is (0.2 M Ammonium acetate, 0.1 M MES pH 6.5, 28% w/v PEG 4,000). The native dataset of WRI1-DNA crystal was collected in Swiss Light Source (SLS). SAD datasets for Se-Met labeled WRI1-DNA crystals were collected at an inflection wavelength of 0.9795 Å at Australian light source (ALS) and Swiss Light Source (SLS). All the datasets were processed using XDS. The Phenix AutoSol program was used for phasing, and 4 selenium atoms were found in the substructure solution (figure of merit: 0.23). The resultant structure served as a template to solve native WRI1-DNA structures by molecular replacement. The models were built and refined using Phenix and Coot. All the structure related figures were generated by PyMol.

Plant Materials

*Arabidopsis* and *N. benthamiana* plants were grown in a growth chamber at 23° C. with a photoperiod of 16 h light (100-150 μmol $m^{-2}$ $se^{-1}$ illumination)/8 h dark. *Arabidopsis* wild-type (Columbia ecotype) and wri1-1 were used in this study. *Arabidopsis* transformation, seed sterilization and germination followed the methods described previously.

Transient Expression in *N. benthamiana*

*Agrobacterium tumefaciens*-mediated transient expression in *N. benthamiana* leaves was conducted as previously described.

Fatty Acid Analysis

Fatty acid analysis of *Arabidopsis* seeds and *N. benthamiana* leaves was done as previously described.

Example 1

The biosynthesis of TAG starts in plastids where the imported pyruvate and glycolytic intermediates are converted to acetyl-coA by pyruvate kinase (PK) and plastidial pyruvate dehydrogenase (PDH), Then, the acetyl-coA is converted into malonyl-coA by acetyl-coA carboxylase (ACCase) in the first committed step of FA synthesis. FAs are assembled on acyl carrier proteins (ACPs) in 7 cycles that add 2 carbons per cycle, following which a fraction of the FAs are further extended and desaturated. Unsaturated and saturated FAs are released from ACPs by acyl-ACP thioesterase A (FATA) and acyl-ACP thioesterase B (FATB), respectively. Free FAs (FFAs) are exported to the ER, where they are sequentially added to glycerol-3-phosphate (G3P) to form TAG. Finally, synthesized TAGs are stored into spherical oil bodies with 0.2 to 0.25 μm in diameter.

Various genes involved in FA de novo biosynthesis (e.g. genes encoding PK and ACCase), are transcriptionally controlled by a 'master regulator' WRI1. *Arabidopsis* WRI1 (AtWRI1) loss-of-function mutant shows significant decrease (~80%) of seed oil content compared to wild-type (WT). WRI1 encodes an APETALA2 (AP2) transcription factor that and displays high expression level in developing seeds. WRI1 binds to a conserved element denoted the AW(ASML1/WRI1)-box—CnTnG(n)7CG, where n represents any nucleotide. Overexpression of WRI1 in *Arabidopsis* and other plant species (e.g. maize and soybean) leads to increased seed oil content, which validates its significant role in mediating oil production.

Figure 3:
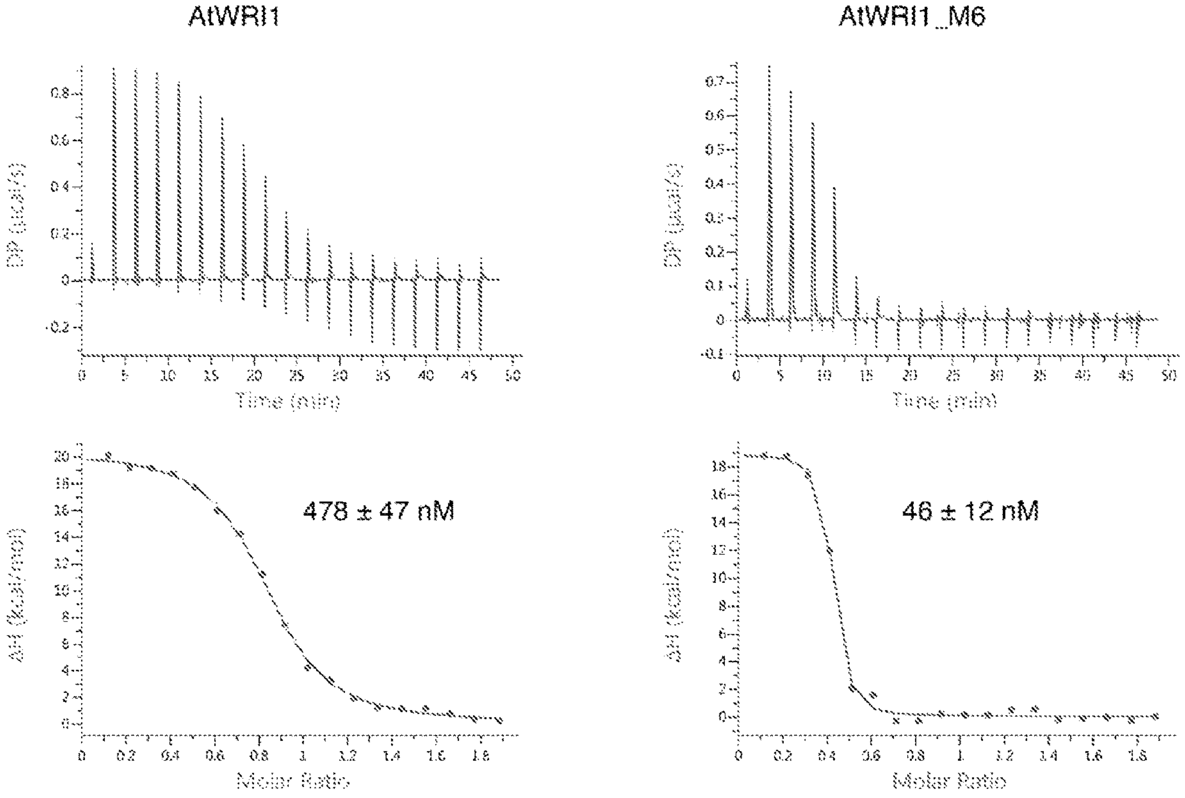
FIG. 3. Binding affinity of native AtWRI1 and engineered AtWRI1_M6 for the cognate promoter DNA. The Kd values of AtWRI1 and AtWRI1_M6 variant (AtWRI1$^{W74R}$) for the DNA are 478±47 nM and 46±12 nm, respectively. The measurement was carried out by ITC (Isothermal Titration Calorimetry).
Figure 4:
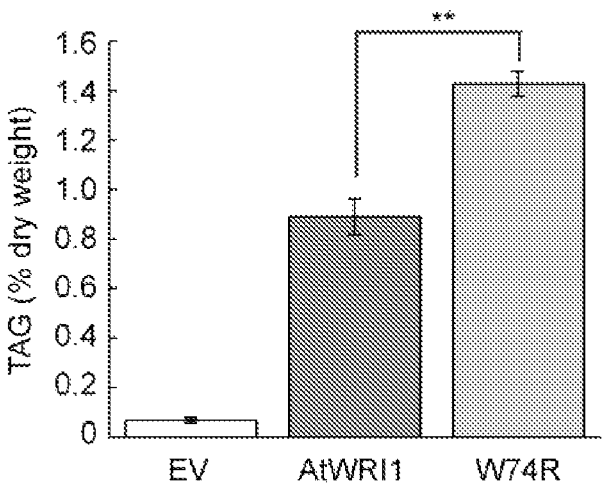
FIG. 4. Triacylglycerol (TAG) content in *N. benthamiana* leaves transiently producing AtWRI1 and AtWRI1_M6 variant. Engineered AtWRI1 variant (AtWRI1_M6 (AtWRI1$^{W74R}$)) shows significant increased TAG production compared to AtWRI1 native form (**P<0.01, t-test).
Figure 5:
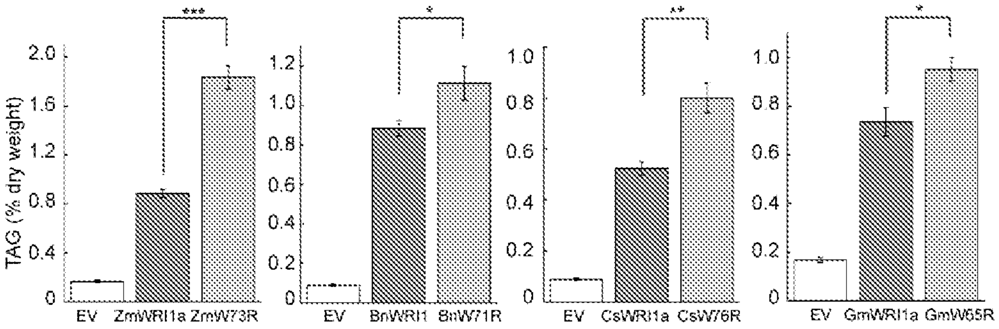
FIG. 5. TAG content in *N. benthamiana* leaves transiently producing diverse WRI1 orthologs and WRI1 variants (with W to R substitution as indicated). "*", "", and "*" indicate significant differences (P<0.05, P<0.01, and P<0.001, respectively, Student's t-test) between WRI1 and WRI1 variants.

The inventors have engineered the wild-type WRI1 polypeptide by a single amino acid substitution (at position 74) to have higher affinity for DNA binding (by over 10 folds), leading to an increase in oil production by over 60% as compared to wild-type polypeptide (see FIG. 3 and FIG. 4). To confirm the significance of the amino acid substitution, the inventors have correspondingly generated the same W to R variants in diverse WRI1 polypeptides from *B. napus, C. sativa, G. max*, and *Z. mays*. As shown in FIG. 5, W to R substitution in WRI1s resulted in substantially enhanced TAG production as well in *N. benthamiana* leaves compared to their corresponding WRI1 native forms.

Figure 6:
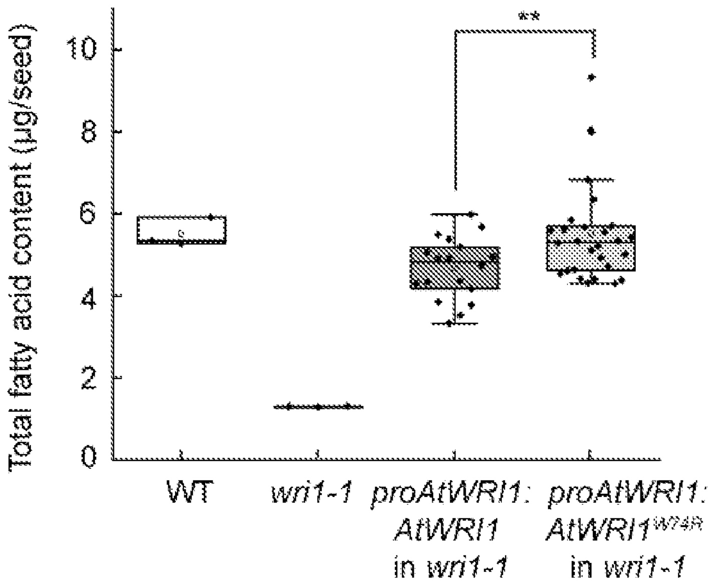
FIG. 6. Total fatty acid content of seeds of WT, wri1-1 and transgenic wri1-1 lines expressing AtWRI1 and AtWRI1$^{W74R}$ under the native promoter of AtWRI1 (proAtWRI1). Difference between values of seed oil content in transgenic wri1-1 lines expressing AtWRI1 and AtWRI1$^{W74R}$ was assessed by Student's t-test. "**" indicate significant difference (P<0.01).
Figure 7:
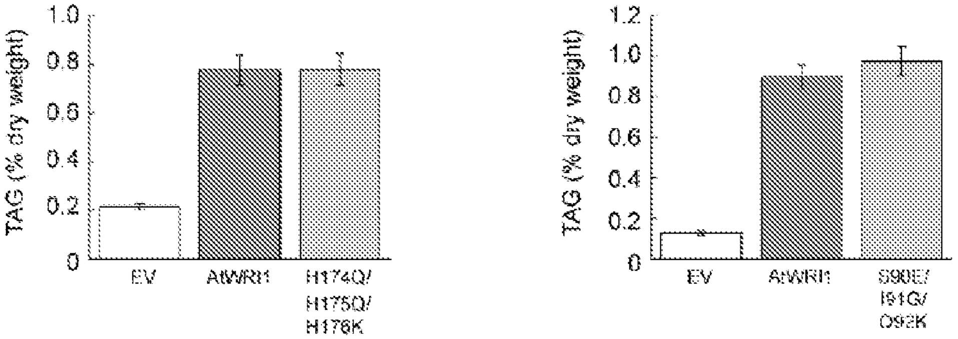
FIG. 7. Triacylglycerol (TAG) content in *N. benthamiana* leaves transiently producing AtWRI1 and AtWRI1 variants. TAG biosynthesis mediated by two AtWRI1 variants which display increased DNA binding affinity as indicated. Results are shown as mean±SE (n=3-4). Empty vector (EV) is used as a control.
Figure 8:
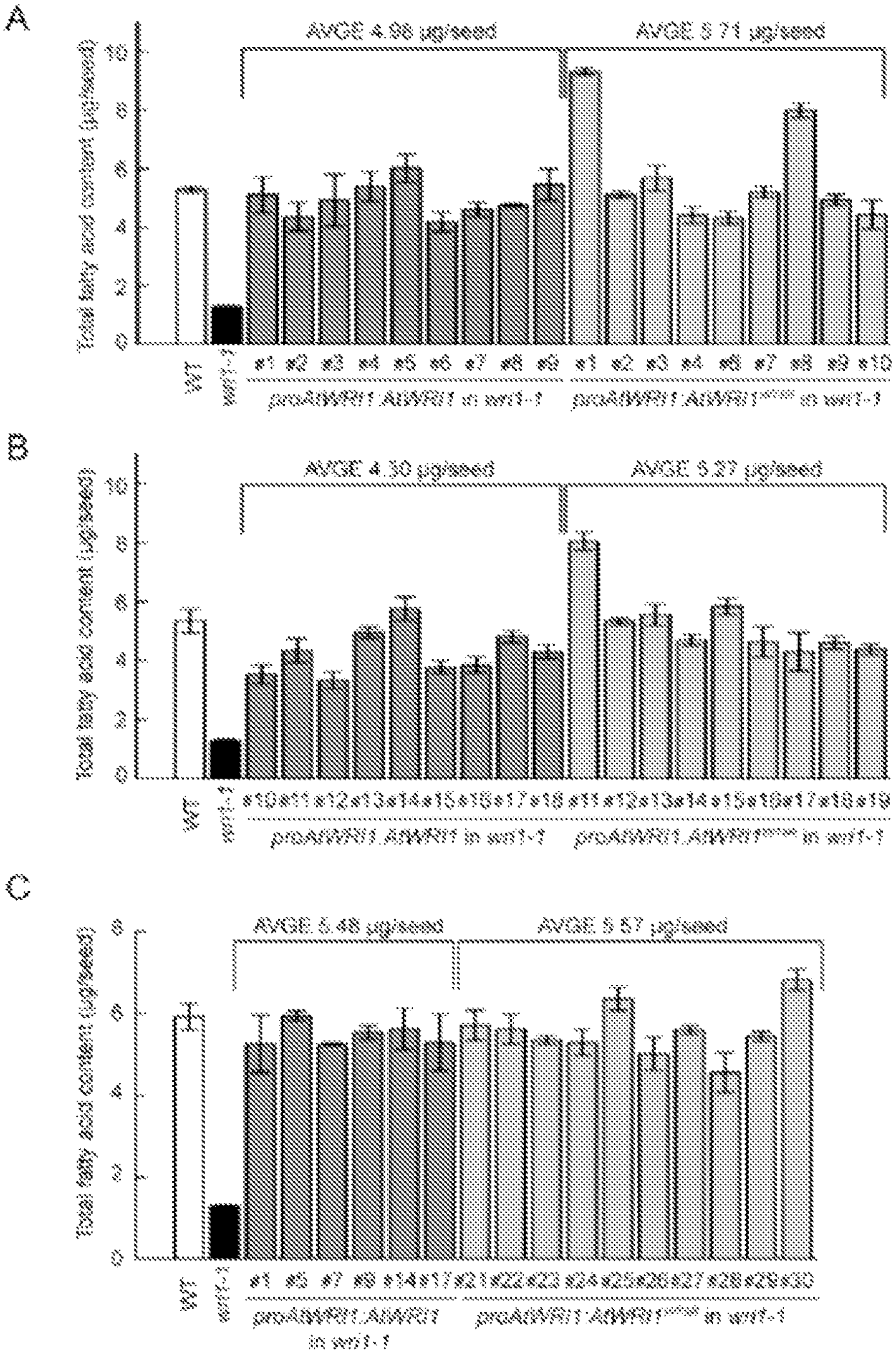
FIG. 8. Total fatty acid content of seeds of WT, wri1-1 and transgenic wri1-1 lines expressing AtWRI1 and AtWRI1$_{W74R}$ under the native promoter of AtWRI1 (proAtWRI1). Results are means±SE (n=2-3) for three independent assays. The average total fatty acid content of transgenic wri1-1 plants expressing AtWRI1 and AtWRI1$_{W74R}$ are designated.

To further verify the effect of W74R of AtWRI1 in plant cells, stable transgenic wri1-1 expressing AtWRI1 and AtWRI1$^{W74R}$ (driven by the native promoter of AtWRI1 (proAtWRI1)) were generated. Compared to transgenic wri1-1 expressing AtWRI1, the seed oil content from multiple transgenic lines was significant enhanced in transgenic wri1-1 expressing AtWRI1$^{W74R}$ (FIG. 6).

Protein sequence in model organism *Arabidopsis*

>AtWRI1-wt (wild type)

(SEQ ID NO: 1)

MKKRLTTSTCSSSPSSSVSSSTTTSSPIQSEAPRPKRAKRAKKSSPSGD

KSHNPTSPASTRRSSIYRGVTRHRWTGRFEAHLWDKSSWNSIQNKKGKQ

VYLGAYDSEEAAAHTYDLAALKYWGPDTILNFPAETYTKELEEMQRVTK

EEYLASLRRQSSGFSRGVSKYRGVARHHHNGRWEARIGRVFGNKYLYLG

TYNTQEEAAAAYDMAAIEYRGANAVTNFDISNYIDRLKKKGVFPFPVNQ

ANHQEGILVEAKQEVETREAKEEPREEVKQQYVEEPPQEEEEKEEEKAE

QQEAEIVGYSEEAAVVNCCIDSSTIMEMDRCGDNNELAWNFCMMDTGFS

PFLTDQNLANENPIEYPELFNELAFEDNIDFMFDDGKHECLNLENLDCC

VVGRESPPSSSSPLSCLSTDSASSTTTTTTSVSCNYLV

>AtWRI1_M6 (M6 variant, W74R)

(SEQ ID NO: 2)

MKKRLTTSTCSSSPSSSVSSSTTTSSPIQSEAPRPKRAKRAKKSSPSGD

KSHNPTSPASTRRSSIYRGVTRHRTGRFEAHLWDKSSWNSIQNKKGKQV

YLGAYDSEEAAAHTYDLAALKYWGPDTILNFPAETYTKELEEMQRVTKE

EYLASLRRQSSGFSRGVSKYRGVARHHHNGRWEARIGRVFGNKYLYLGT

YNTQEEAAAAYDMAAIEYRGANAVTNFDISNYIDRLKKKGVFPFPVNQA

NHQEGILVEAKQEVETREAKEEPREEVKQQYVEEPPQEEEEKEEEKAEQ

QEAEIVGYSEEAAVVNCCIDSSTIMEMDRCGDNNELAWNFCMMDTGFSP

FLTDQNLANENPIEYPELFNELAFEDNIDFMFDDGKHECLNLENLDCCV

VGRESPPSSSSPLSCLSTDSASSTTTTTTSVSCNYLV

Other variants

>AtWRI1 (S90E/I91G/Q92K)

(SEQ ID NO: 3)

MKKRLTTSTCSSSPSSSVSSSTTTSSPIQSEAPRPKRAKRAKKSSPSGD

KSHNPTSPASTRRSSIYRGVTRHRWTGRFEAHLWDKSSWNEGKNKKGKQ

VYLGAYDSEEAAAHTYDLAALKYWGPDTILNFPAETYTKELEEMQRVTK

EEYLASLRRQSSGFSRGVSKYRGVARHHHNGRWEARIGRVFGNKYLYLG

TYNTQEEAAAAYDMAAIEYRGANAVTNFDISNYIDRLKKKGVFPFPVNQ

ANHQEGILVEAKQEVETREAKEEPREEVKQQYVEEPPQEEEEKEEEKAE

-continued

QQEAEIVGYSEEAAVVNCCIDSSTIMEMDRCGDNNELAWNFCMMDTGFS
PFLTDQNLANENPIEYPELFNELAFEDNIDFMFDDGKHECLNLENLDCC
VVGRESPPSSSSPLSCLSTDSASSTTTTTTSVSCNYLV

>AtWRI1 (H174Q/H175Q/H176K)
(SEQ ID NO: 4)

MKKRLTTSTCSSSPSSSVSSSTTTSSPIQSEAPRPKRAKRAKKSSPSGD
KSHNPTSPASTRRSSIYRGVTRHRWTGRFEAHLWDKSSWNSIQNKKGKQ
VYLGAYDSEEAAAHTYDLAALKYWGPDTILNFPAETYTKELEEMQRVTK
EEYLASLRRQSSGFSRGVSKYRGVARQQKNGRWEARIGRVFGNKYLYLG
TYNTQEEAAAAYDMAAIEYRGANAVTNFDISNYIDRLKKKGVFPFPVNQ
ANHQEGILVEAKQEVETREAKEEPREEVKQQYVEEPPQEEEEKEEEKAE
QQEAEIVGYSEEAAVVNCCIDSSTIMEMDRCGDNNELAWNFCMMDTGFS
PFLTDQNLANENPIEYPELFNELAFEDNIDFMFDDGKHECLNLENLDCC
VVGRESPPSSSSPLSCLSTDSASSTTTTTTSVSCNYLV

DNA sequence
BCCP2(-34/-11) promoter sequences that WRI1 binds to
(SEQ ID NO: 5)

TACTTCCTCGGTTTCATCGTCCAC (SEQ ID NO: 6)

ATGAAGGAGCCAAAGTAGCAGGTG

TABLE 1

The binding affinities of wild-type (WT) AtWRI1 and its mutants to the DNA by ITC assay.

| AtWRI1 | $K_D$ (μM) |
|---|---|
| WT | 0.48 ± 0.05 |
| H72A | 1.74 ± 0.17 |
| E79A | 0.94 ± 0.14 |
| Q98A | 4.37 ± 0.95 |
| H175A | 2.00 ± 0.79 |
| E181A | 4.62 ± 0.58 |
| R183A | n.b. |
| Y192E | n.b. |
| S90E/I91G/Q92K | 0.24 ± 0.05 |
| H174Q/H175Q/H176K | 0.16 ± 0.20 |
| W74R | 0.05 ± 0.01 |

Note:
n.b, not binding

Variants in Other Economic Crops

Figure 9:
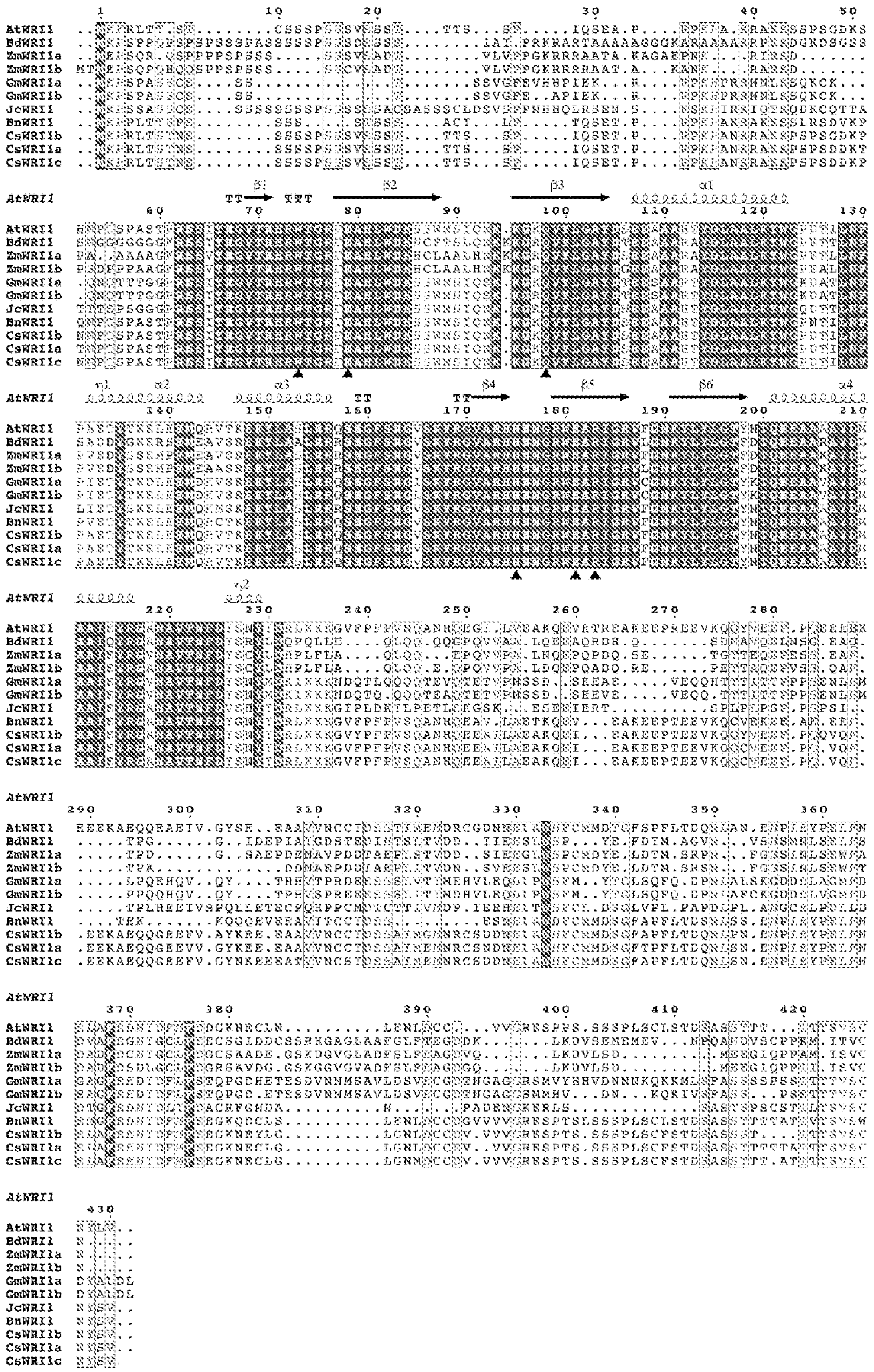
FIG. 9. Sequence alignment of WRI1 orthologs from diverse plant species. DNA binding regions are quite conserved. The protein sequences of WRI1 from *Arabidopsis thaliana* (At), *Brachypodium distachyon* (Bd, BdWRI1: SEQ ID NO:14), *Brassica napus* (Bn, BnWRI1: SEQ ID NO: 7), *Camelina sativa* (Cs, CsWRI1a: SEQ ID NO: 11, CsWRI1b: SEQ ID NO: 12, CsWRI1c: SEQ ID NO: 13), *Glycine max* (Gm, GmWRI1a: SEQ ID NO: 15, GmWRI1b: SEQ ID NO: 16), *Jatropha curcas* (Jc, JcWRI1: SEQ ID NO: 10), and *Zea mays* (Zm, ZmWRI1a: SEQ ID NO: 8, ZmWRI1b: SEQ ID NO: 9), were aligned. The secondary structure elements were shown according to the structure of AtWRI1. The conserved amino acids responsible for specific DNA binding were marked by triangles (The three WRI1 variants (M6 variant, W74R; S90E/I91G/Q92K; H174Q/H175Q/H176K) are indicated by triangles, respectively).
Figure 10:
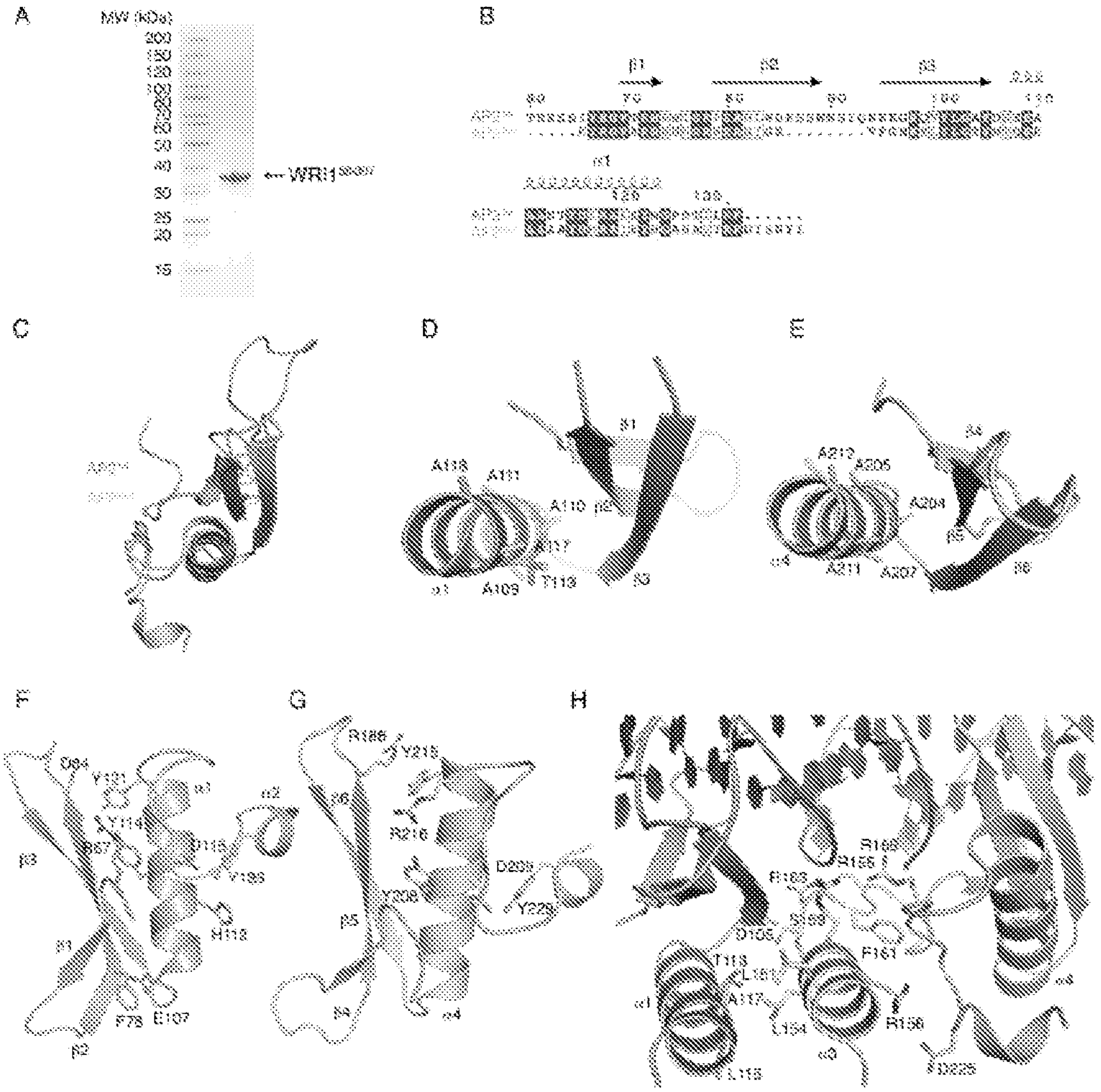
FIG. 10. Purification of WRI$^{158-307}$, structural comparison of the two AP2 domains, and the domain assembly in WRI1. A) SDS-PAGE check of the purified WRI1$^{58-307}$. B) Sequence alignment of the two AP2 domains in WRI1 (AP2$^{1st}$: positions 60 to 130 of SEQ ID NO: 1 and AP2$^{2nd}$: positions 167 to 229 of SEQ ID NO: 1). C) Structural comparison of the two AP2 domains. D) and E) The hydrophobic cores inside the first AP2 domain (C) and the second AP2 domain (D). F) and G) The stabilization of the two AP2 domains. H) The linker region connects two AP2 domains and interacts with DNA. The interacting amino acids are shown in sticks.
Figure 11:
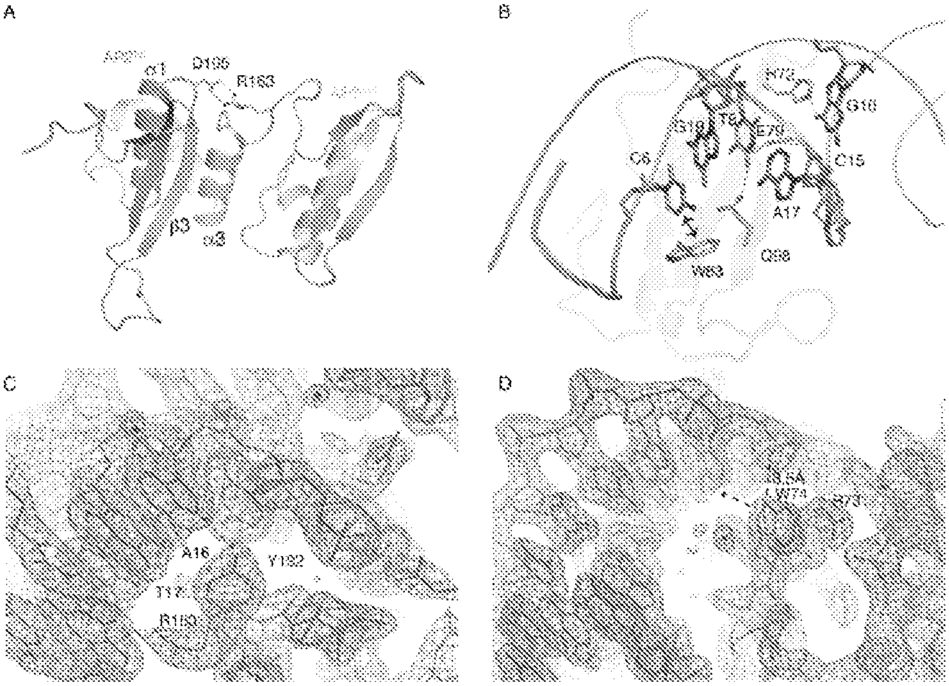
FIG. 11. Structure of WRI1-DNA complex. A) The salt bridge formed between R163 in the linker region and D105 from the 1$^{st}$ AP2 domain. The salt bridge is indicated by the dashed lines. B) The W83 forms Pi-Pi interaction with the 5'C6. The Pi-Pi interaction is indicated by a double-ended arrow. C) The Y192 interacts with 5'A16T17, but not the conserved AW motif nucleotide (such as A16 can be substituted by G at this position). The blue mesh indicates the electron density map (2Fo-Fc) contoured at 1.2 rmsd (root-mean-square-deviation). The dashed line indicates the interaction between Y192 and 5'A16. D) The residue W74 is in close vicinity to ds-DNA. The W74 and R73 are labelled, and the distance between W74 and the nearest backbone phosphate is indicated. W74 can also potentially form additional interaction with nucleotides, which is indicated by the dashed arrow. The mesh indicates the electron density map (2Fo-Fc) contoured at 1.2 rmsd.

Given the well-known conservation of WRI1's function, the above variants and the combination for the orthologs in other economic crops, including *Arabidopsis thaliana* (At), *Brachypodium distachyon* (Bd), *Brassica napus* (Bn), soybean (*Glycine max*, Gm), *Jatropha curcas* (Jc), maize (*Zea mays*, Zm) and camelina (*Camelina sativa*, Cs) is shown in FIG. 9.

An amino acid substitution at a position corresponding to position 74 as set forth in SEQ ID NO: 1 (i.e. WRI1 from *Arabidopsis thaliana* (At)) can also be made in the orthologs as shown in bold and underlined below. The amino acid substitution can be an amino acid substitution to a positively charged amino acid.

>BnWRI1
(SEQ ID NO: 7)

MKRPLTTSPSSSSSTSSSACILPTQSETPRPKRAKRAKKSSLRSDVKPQ
NPTSPASTRRSSIYRGVTRHRWTGRYEAHLWDKSSWNSIQNKKGKQVYL
GAYDSEEAAAHTYDLAALKYWGPNTILNFPVETYTKELEEMQRCTKEEY
LASLRRQSSGFSRGVSKYRGVARHHHNGRWEARIGRVFGNKYLYLGTYN
TQEEAAAAYDMAAIEYRGANAVTNFDIGNYIDRLKKKGVFPFPVSQANH
QEAVLAETKQEVEAKEEPTEEVKQCVEKEEAKEEKTEKKQQQEVEEAVI
TCCIDSSESNELAWDFCMMDSGFAPFLTDSNLSSENPIEYPELFNEMGF
EDNIDFMFEEGKQDCLSLENLDCCDGVVVVGRESPTSLSSSPLSCLSTD
SASSTTTTATTVTSVSWNYSV

>ZmWRI1a
(SEQ ID NO: 8)

MERSQRQSPPPPSPSSSSSSVSADTVLVPPGKRRRAATAKAGAEPNKRI
RKDPAAAAAGKRSSVYRGVTRHRWTGRFEAHLWDKHCLAALHNKKKGRQ
VYLGAYDSEEAAARAYDLAALKYWGPETLLNFPVEDYSSEMPEMEAVSR
RRSSGFSRGVSKYRGVARHHHNGRWEARIGRVFGNKYLYLGTFDTQEEA
AEEYLASLRKAYDLAAIEYRGVNAVTNFDISCYLDHPLFLAQLQQEPQV
VPALNQEPQPDQSETGTTEQEPESSEAKTPDGSAEPDENAVPDDTAEPL
STVDDSIEEGLWSPCMDYELDTMSRPNFGSSINLSEWFADADFDCNIGC
LFDGCSAADEGSKDGVGLADFSLFEAGDVQLKDVLSDMEEGIQPPAMIS
VCN

>ZmWRI1b
(SEQ ID NO: 9)

MTMERSQPQHQQSPPSPSSSSSCVSADTVLVPPGKRRRRAATAKANKRA
RKDPSDPPPAAGKRSSVYRGVTRHRWTGRFEAHLWDKHCLAALHNKKKG
RQVYLGAYDGEEAAARAYDLAALKYWGPEALLNFPVEDYSSEMPEMEAA
SREEYLASLRRRSSGFSRGVSKYRGVARHHHNGRWEARIGRVLGNKYLY
LGTFDTQEEAAKAYDLAAIEYRGANAVTNFDISCYLDHPLFLAQLQQEQ
PQVVPALDQEPQADQREPETTAQEPVSSQAKTPADDNAEPDDIAEPLIT
VDNSVEESLWSPCMDYELDTMSRSNFGSSINLSEWFTDADFDSDLGCLF
DGRSAVDGGSKGGVGVADFSLFEAGDGQLKDVLSDMEEGIQPPTIISVC
N

>JcWRI1
(SEQ ID NO: 10)

MKRSSASSCSSSSSSSSSPSSSSSSACSASSSCLDSVSPPNHHQLRSEN
SKSKRIRKIQTKQDKCQTTATTTSPSGGGRRSSIYRGVTRHRWTGRFEA
HLWDKSSWNNIQNKKGRQVYLGAYDNEEAAAHTYDLAALKYWGQDTTLN
FLIETYSKELEEMQKMSKEEYLASLRRRSSGFSRGVSKYRGVARHHHNG
RWEARIGRVFGNKYLYLGTYNTQEEAAAAYDMAAIEYRGANAVTNFDVS
HYIDRLKKKGIPLDKILPETLSKGSKESEEIERTSPLPLPSPPSPSITP
LHEEIVSPQLLETECPQHPPCMDTCTTIVMDPIEEHELTWSFCLDSGLV

-continued

PLPAPDLPLANGCELPDLLDDTGFEDNIDLIFDACRFGNDANPADENGK

ERLSSASTSPSCSTTLTSVSCNYSV

>CsWRI1a (SEQ ID NO: 11)

MKRRLTSTNSSSSSPSSSVSSSTTTSSPIQSETPRPKRANKRAKKPSPS

DDKTTNPTSPASTRRSSIYRGVTRHRWTGRFEAHLWDKSSWNSIQNKKG

KQVYLGAYDSEEAAAHTYDLAALKYWGPDTILNFPAETYTKELEEMQRV

TKEEYLASLRRQSSGFSRGVSKYRGVARHHHNGRWEARIGRVFGNKYLY

LGTYNTQEEAAAAYDMAAIEYRGANAVTNFDISNYIDRLKKKGVFPFPV

SQANHQEEAILAEAKQEIEAKEEPTEEVKQQCVEEPPQVQKEEKAEQQG

EEVVGYKEEEAAVVNCCIDSSAIMEMNRCSNDNELAWNFCMMDSGFTPF

LTDQNLSNENPIEYPELFNELAFEENIDFMFEEGKNECLGLGNLDCCEV

VVGRESPTSSSSPLSCFSTDSASSTTTTTATTTSVSCNYSV

>CsWRI1b (SEQ ID NO: 12)

MKRRLTSTNSSSSSPSSSVSSSTTTSSPIQSETPRPKRANKRAKKPSPS

GDKPNNPTSPASTRRSSIYRGVTRHRWTGRFEAHLWDKSSWNSIQNKKG

KQVYLGAYDSEEAAAHTYDLAALKYWGPDTILNFPAETYTKELEEMQRV

TKEEYLASLRRQSSGFSRGVSKYRGVARHHHNGRWEARIGRVFGNKYLY

LGTYNTQEEAAAAYDMAAIEYRGANAVTNFDISNYIDRLKKKGVYPFPV

SQANHQEEAILAEAKQEIEAKEEPTEEVKQQYVEEPPQQVQKEEKAEQQ

GEEFVAYKEEEAAVVNCCIDSSAIMGMNRCSDDNELAWNFCMMDSGFAP

FLTDQNLPNENPIEYPELFNELAFEENIDFMFEEGKNEYLGLGNLDCCD

VVVVGRESPTSSSSPLSCFSTDSASSSTTTTSVSCNYSV

>CsWRI1c (SEQ ID NO: 13)

MKRRLTSTNSSSSSPSSSVSSSTTTSSPIQSETPRPKRANKRAKKPSPS

DDKPNNPTSPASTRRSSIYRGVTRHRWTGRFEAHLWDKSSWNSIQNKKG

KQVYLGAYDSEEAAAHTYDLAALKYWGPDTILNFPAETYTKELEEMQRV

TKEEYLASLRRQSSGFSRGVSKYRGVARHHHNGRWEARIGRVFGNKYLY

LGTYNTQEEAAAAYDMAAIEYRGANAVTNFDISNYIDRLKKKGVFPFPV

SQANHQEEAILAEAKQEIEAKEEPTEEVKQQCVEEPPQVQKEEKAEQQG

EEFVGYNKEEEATVVNCSIDSSAIMEMNRCSDDNELAWNFCMMDSGFAP

FLTDQNLSNENPIEYPELFNELAFEENIDFMFEEGKNECLGLGNMDCCD

VVVVGRESPTSSSSPLSCFSTDSASSTTTATTTTSVSCNYSV

>BdWRI1

(SEQ ID NO: 14)

MKRSPPQPSPSPSSSPASSSSSPSSSDSSSSIAIPRKRARTAAAAAGGG

KARAAAAKRPKKDGKDSGSSSNGGGGGGGKRSSIYRGVTRHRWTGRFEA

-continued

HLWDKNCFTSLQNKKKGRQVYLGAYDTEEAAARAYDLAALKYWGPETTL

NFSADDYGKERSEMEAVSREEYLAALRRRSSGFSRGVSKYRGVARHHHN

GRWEARIGRVLGNKYLYLGTFDTQEEAARAYDLAAIQYRGANAVTNFDI

SRYLDQPQLLEQLQQQQGPQVVAALQEEAQRDHQSDNAVQELNSGEAQT

PGGIDEPIAIGDSTEDINTSLTVDDIIEESLWSPYEFDIMAGVNVSNSM

NLSELFSDVAFEGNIGCLFEECSGIDDCSSRHGAGLAAFGLFTEGDDKL

KDVSEMEMEVNPQANDVSCPPKMITVCN

>GmWRI1a (SEQ ID NO: 15)

MKRSPASSCSSSTSSVGFEVHHPIEKRRPKHPRRNNLKSQKCKQNQTTT

GGRRSSIYRGVTRHRWTGRFEAHLWDKSSWNNIQSKKGKQVYLGAYDTE

ESAARTYDLAALKYWGKDATLNFPIETYTKDLEEMDKVSREEYLASLRR

QSSGFSRGISKYRGVARHHHNGRWEARIGRVCGNKYLYLGTYKTQEEAA

VAYDMAAIEYRGVNAVTNFDISNYMDKIKKKNDQTLQQQQTEVQTETVP

NSSDSEEAEVEQQHTTTITTPPPSENLHMLPQEHQVQYTHHVTPRDEES

SSLVTIMEHVLEQDLPWSFMYTGLSQFQDPNLALSKGDDDLAGMFDGAG

FEEDIDFLESTQPGDHETESDVNNMSAVLDSVECGDTNGAGGRSMVYHH

VDNNNKQKKMLSFASSSSPSSTTTTVSCDYALDL

>GmWRI1b (SEQ ID NO: 16)

MKRSPASSCSSSTSSVGFEAPIEKRRPKHPRRNNLKSQKCKQNQTTTGG

RRSSIYRGVTRHRWTGRFEAHLWDKSSWNNIQSKKGRQVYLGAYDTEES

AARTYDLAALKYWGKDATLNFPIETYTKELEEMDKVSREEYLASLRRQS

SGFSRGLSKYRGVARHHHNGRWEARIGRVCGNKYLYLGTYKTQEEAAVA

YDMAAIEYRGVNAVTNFDISNYMDKIKKKNDQTQQQQTEAQTETVPNSS

DSEEVEVEQQTTTITTPPPSENLHMPPQQHQVQYTPHVSPREEESSSLI

TIMDHVLEQDLPWSFMYTGLSQFQDPNLAFCKGDDDLVGMFDSAGFEED

IDFLFSTQPGDETESDVNNMSAVLDSVECGDTNGAGGSMMHVDNKQKIV

SFASSPSSTTTVSCDYALDL

AP2 region of WRI1

AP2 region of WRI1 functions as DNA binding domain of WRI1 transcription factor. AP2 region of WRI1 binds to the cis-element, AW-box, in promoters of WRI1 target genes involved in fatty acid biosynthesis. Enhancing binding affinity of AP2 of AtWRI1 (i.e., AtWRI1$^{55-255}$) leads to oil yield increase. The AP2 region of WRI1 is conserved across AtWRI1 and WRI1 orthologs identified in other plant species. Therefore, the invention also includes WRI1 orthologs from other plant species with at least one amino acid substitution. For example, the WRI1 orthologs comprise an AP2 region having amino acid sequence having at least 70% sequence identity to the AP2 region of wild-type WRI1 polypeptide (i.e. AtWRI1$^{55-255}$).

The invention claimed is:

1. An isolated polynucleotide encoding a polypeptide that is distinguished from a wild-type Wrinkled1 polypeptide by at least one amino acid substitution in the wild-type Wrinkled1 amino acid sequence, wherein the amino acid sequence of the wild-type Wrinkled1 polypeptide has at least 95% identity to SEQ ID NO: 1 and wherein the at least one amino acid substitution comprises an amino acid substitution of arginine or lysine at a position corresponding to position 74 in SEQ ID NO: 1, the polypeptide increases the oil content in a plant.

2. The polynucleotide of claim 1, wherein the wild-type Wrinkled1 polypeptide has an amino acid sequence having at least 95% sequence identity to the AP2 region (positions 55-255) of SEQ ID NO: 1.

3. The polynucleotide of claim 1, wherein the at least one amino acid substitution further comprises at least one amino acid substitution at a position corresponding to position 90, 91 and/or 92 as set forth in SEQ ID NO: 1.

4. The polynucleotide of claim 3, wherein the amino acid residue at position 90 is substituted with a glutamic or aspartic acid, the amino acid residue at position 91 is substituted with a glycine and/or the amino acid residue at position 92 is substituted with a lysine or an arginine.

5. The polynucleotide of claim 1, wherein the at least one amino acid substitution further comprises at least one amino acid substitution at a position corresponding to positions 174, 175 and/or 176 as set forth in SEQ ID NO: 1.

6. The polynucleotide of claim 5, wherein the amino acid residues at positions 174 and 175 are each independently substituted with a glutamine and/or the amino acid residue at position 176 is substituted with a lysine.

7. A polypeptide encoded by the isolated polynucleotide of claim 1.

8. A construct comprising the isolated polynucleotide of claim 1.

9. A vector comprising the construct of claim 8.

10. A method of preparing a transgenic plant cell, the method comprising transforming a plant cell with the construct of claim 8 or the vector of claim 9.

11. A transgenic plant, plant cell or plant seed comprising the polynucleotide of claim 1 or the construct of claim 8.

* * * * *